United States Patent
Morgan et al.

(10) Patent No.: US 10,799,330 B2
(45) Date of Patent: Oct. 13, 2020

(54) MULTI-LUMEN SHEATH CENTRAL VENOUS CATHETER WITH VENA CAVA FILTER APPARATUS AND METHOD OF USING SAME

(71) Applicant: BiO2 Medical, Inc., San Antonio, TX (US)

(72) Inventors: Jeremy Morgan, Idaho Springs, CO (US); Daniel D. Sims, Arvada, CO (US); Jeffrey N. Steinmetz, Arvada, CO (US)

(73) Assignee: Mermaid Medical Vascular ApS, Stenlose (DK)

( * ) Notice: Subject to any disclaimer, the term of this patent is extended or adjusted under 35 U.S.C. 154(b) by 0 days.

(21) Appl. No.: 13/935,306

(22) Filed: Jul. 3, 2013

(65) Prior Publication Data
US 2014/0018840 A1    Jan. 16, 2014

Related U.S. Application Data

(60) Provisional application No. 61/668,308, filed on Jul. 5, 2012.

(51) Int. Cl.
*A61F 2/01* (2006.01)

(52) U.S. Cl.
CPC ............... *A61F 2/01* (2013.01); *A61F 2/013* (2013.01); *A61F 2002/016* (2013.01);
(Continued)

(58) Field of Classification Search
CPC ........ A61F 2007/006; A61F 2007/0095; A61F 7/0085; A61F 2007/0078; A61F 2/013;
A61F 2/01; A61F 2230/008; A61F 2230/0093; A61F 2230/0006; A61F 2230/0071; A61F 2230/0067; A61F 2230/0091; A61F 2230/097;
(Continued)

(56) References Cited

U.S. PATENT DOCUMENTS

| 6,511,492 B1 * | 1/2003 | Rosenbluth | A61B 17/22032 606/159 |
| 6,582,396 B1 * | 6/2003 | Parodi | A61B 17/12 604/101.04 |

(Continued)

FOREIGN PATENT DOCUMENTS

| EP | 0 430 848 | 12/1993 | ............... A61F 2/02 |
| WO | WO 1997/027808 | 8/1997 | ............ A61B 17/22 |

(Continued)

OTHER PUBLICATIONS

Decousus, Nerve, et al., "A clinical trial of vena caval filters in the prevention of pulmonary embolism in patients with proximal deep-vein thrombisis" *The New England Journal of Medicine* 338(7): 409-415 (Feb. 12, 1998).
(Continued)

*Primary Examiner* — Shaun L David
*Assistant Examiner* — Mohamed G Gabr
(74) *Attorney, Agent, or Firm* — David G. Rosenbaum; Benjamin D. Rotman; Rosenbaum IP, P.C.

(57) ABSTRACT

A combined multi-lumen sheath with a wire body and a filter. The filter may be removably coupled to the multi-lumen sheath within a filter capsule for temporary placement and retrieval.

11 Claims, 19 Drawing Sheets

(52) U.S. Cl.
CPC . *A61F 2002/018* (2013.01); *A61F 2230/0006* (2013.01); *A61F 2230/008* (2013.01); *A61F 2230/0067* (2013.01); *A61F 2230/0097* (2013.01)

(58) Field of Classification Search
CPC .......... A61F 2002/016; A61F 2002/018; A61F 2002/011; A61F 2240/001; A61M 2025/0036; A61M 2025/0003; A61M 2025/004; A61M 2025/0042; A61M 2025/0183; A61M 2025/0681; A61M 2025/1052; A61M 2205/3523; A61M 25/0029; A61M 25/0009; A61M 2025/01; A61B 17/221; A61B 17/22; A61B 2017/2212; A61B 2017/12054; A61B 2017/12095; A61B 2017/22044
USPC .......................................... 606/200
See application file for complete search history.

(56) References Cited

U.S. PATENT DOCUMENTS

| | | | |
|---|---|---|---|
| 8,057,496 B2 | 11/2011 | Fischer, Jr. .................. | 606/159 |
| 2006/0203769 A1 | 9/2006 | Saholt et al. ................. | 370/329 |
| 2007/0129753 A1* | 6/2007 | Quinn ............... | A61B 17/0057 |
| | | | 606/200 |
| 2008/0221587 A1* | 9/2008 | Schwartz ............. | A61B 17/221 |
| | | | 606/113 |
| 2008/0255595 A1 | 10/2008 | Buchbinder et al. ......... | 606/159 |
| 2009/0062840 A1* | 3/2009 | Angel ..................... | A61F 2/013 |
| | | | 606/200 |
| 2010/0217304 A1 | 8/2010 | Angel et al. .................. | 606/200 |

FOREIGN PATENT DOCUMENTS

| | | | | |
|---|---|---|---|---|
| WO | WO 1998/050103 | 11/1998 | ............ | A61M 29/00 |
| WO | WO 2004/091711 | 10/2004 | ............ | A61M 25/10 |
| WO | WO 2009/029861 | 3/2009 | ............. | A61M 5/00 |
| WO | WO 2011/085266 | 7/2011 | ............. | A61M 5/00 |

OTHER PUBLICATIONS

Lin, Peter H., et al., "Vena caval filters in the treatment of acute DVT" *Endovascular Today* pp. 40-50 (Jan. 2005).
International Search Report issued in corresponding foreign application, PCT/US2013/049380, pp. 1-6 (dated Nov. 4, 2013).
Written Opinion issued in corresponding foreign application, PCT/US2013/049380, pp. 1-5 (dated Nov. 4, 2013).
International Preliminary Report on Patentability issued in corresponding foreign application, PCT/US2013/049380, pp. 1-7 (dated Jan. 15, 2015).
European Search Report issued in a corresponding foreign application, pp. 1-8 (dated Feb. 29, 2016).

* cited by examiner

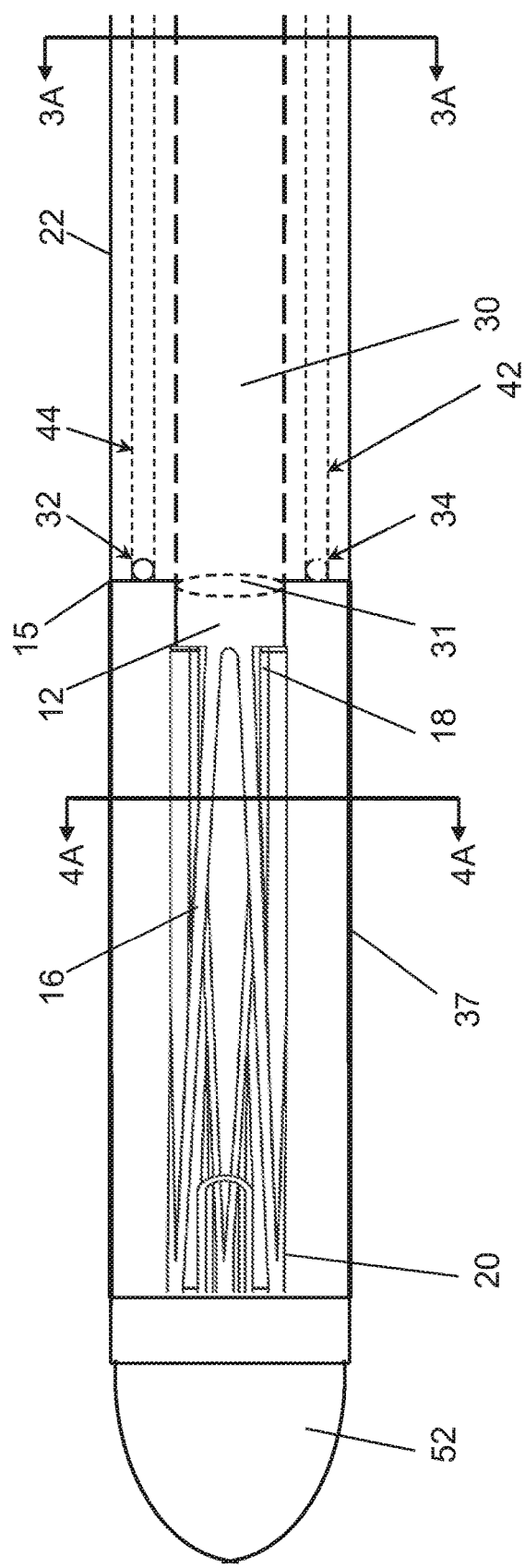
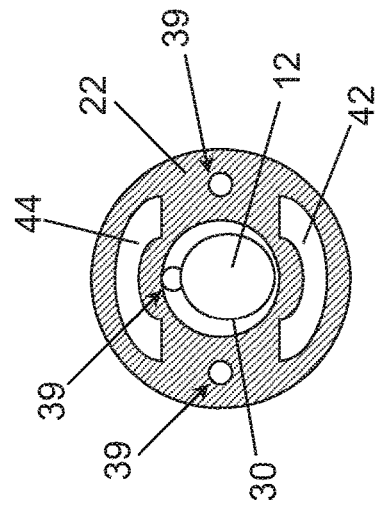
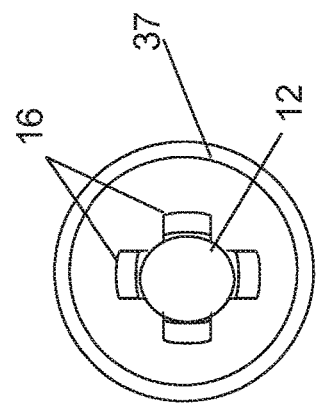
FIG. 2A
FIG. 3A
FIG. 4A

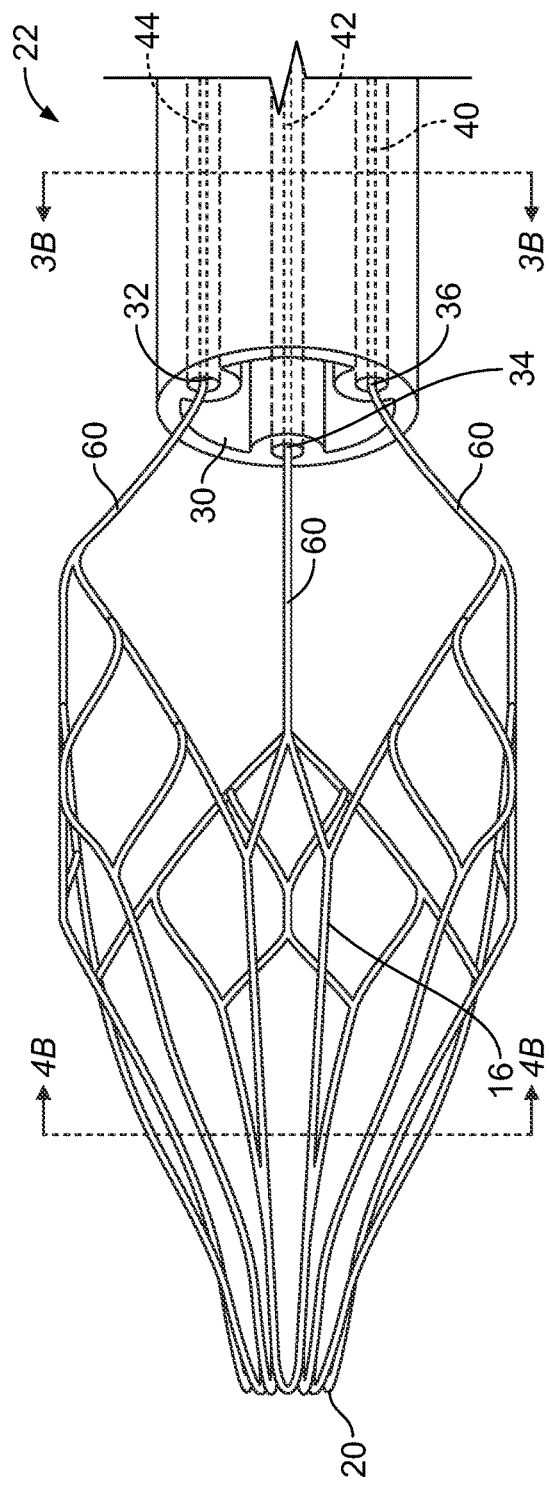
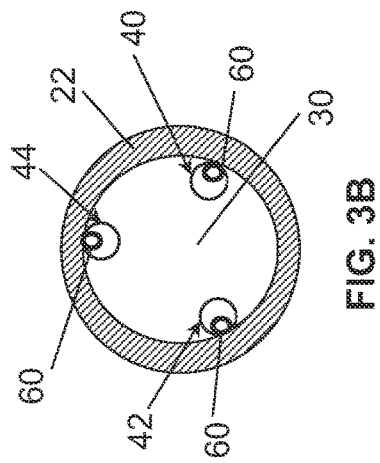
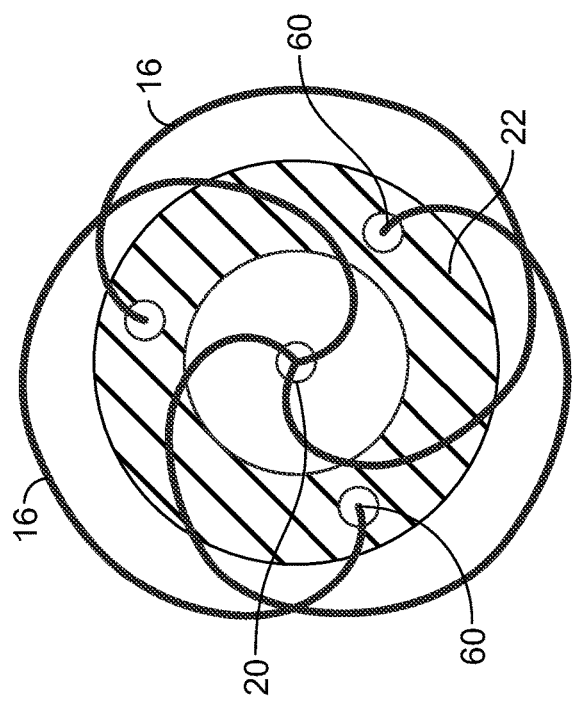

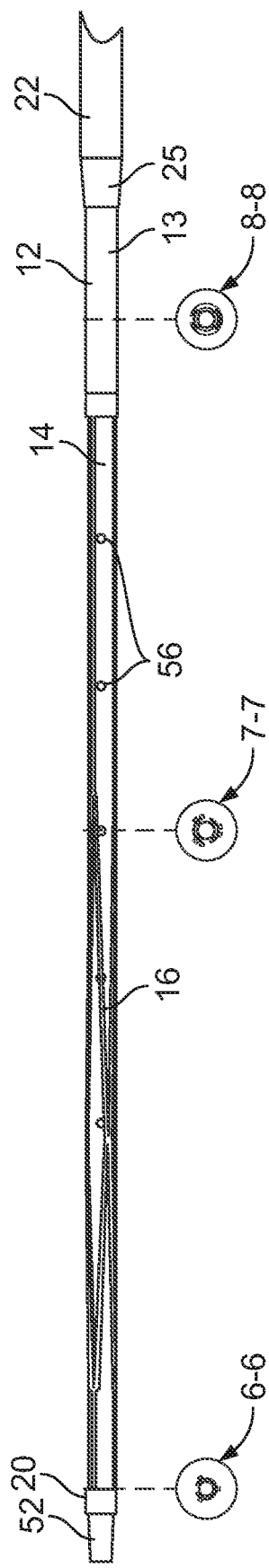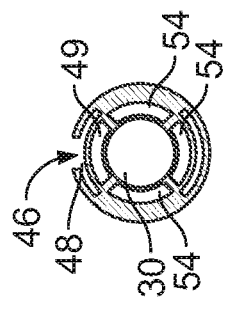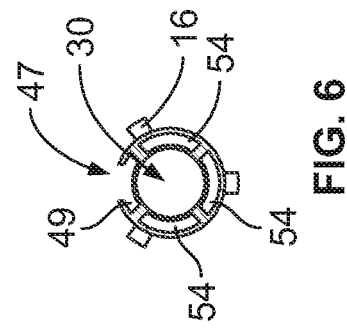

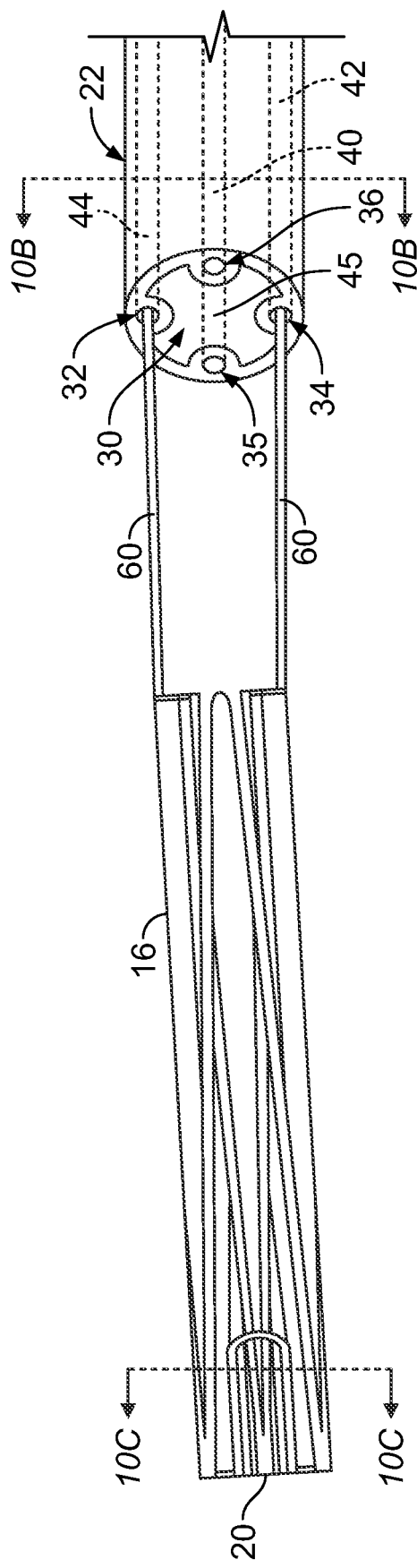
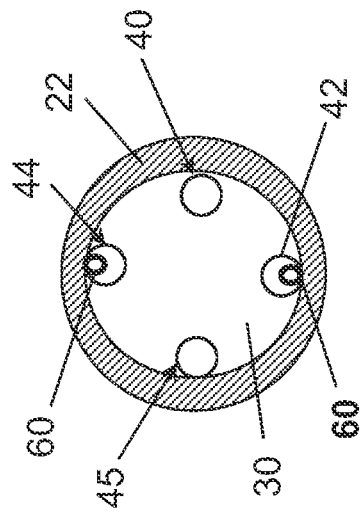
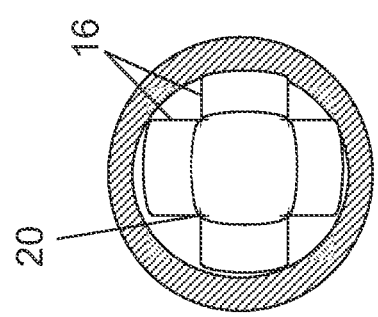
FIG. 10A
FIG. 10B
FIG. 10C

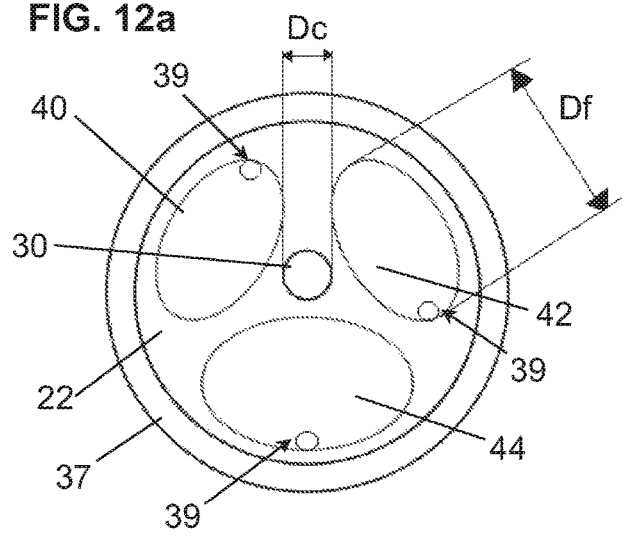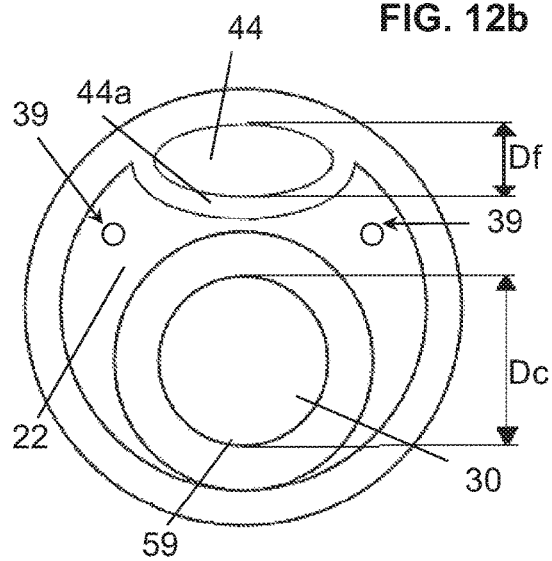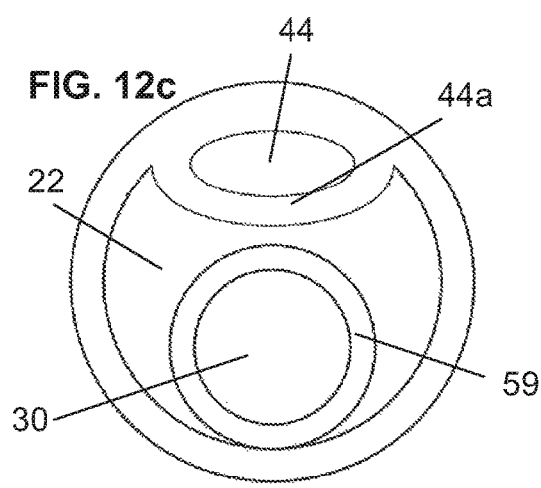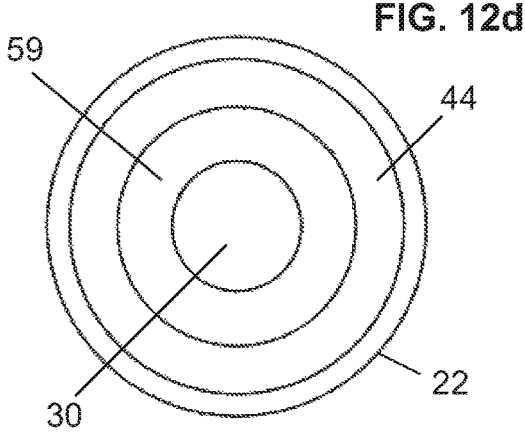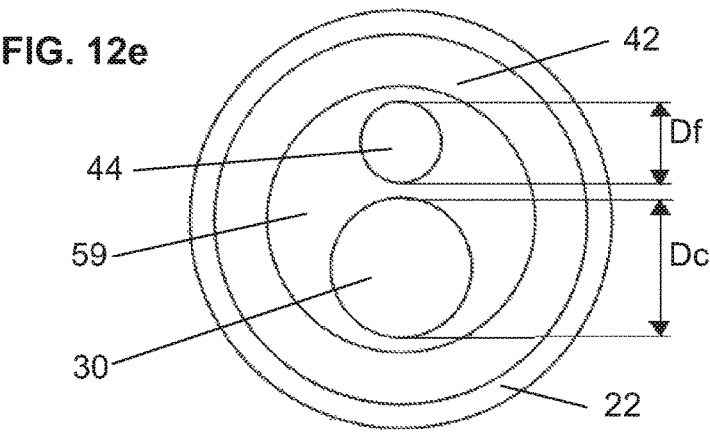

FIG. 18A
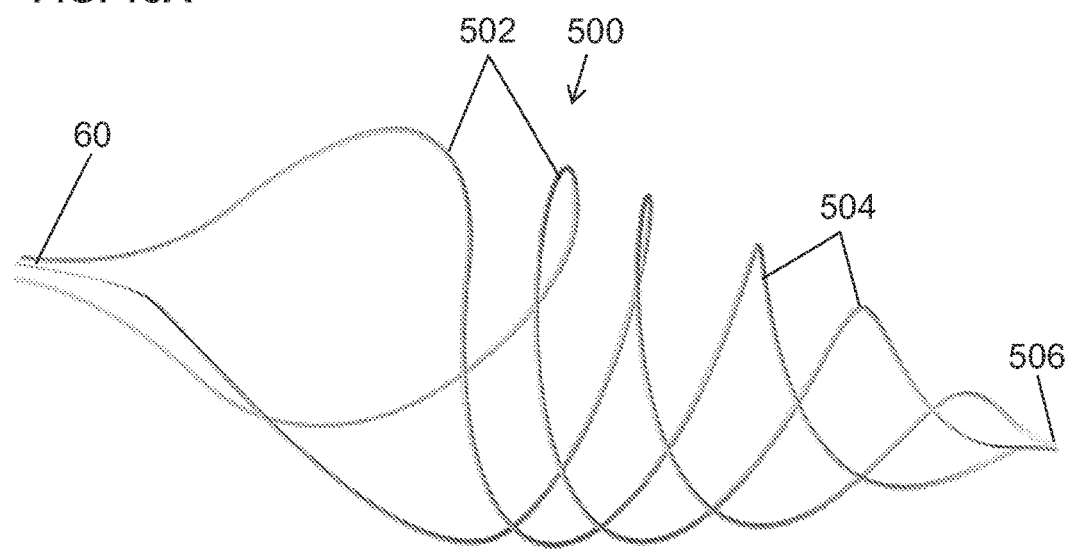
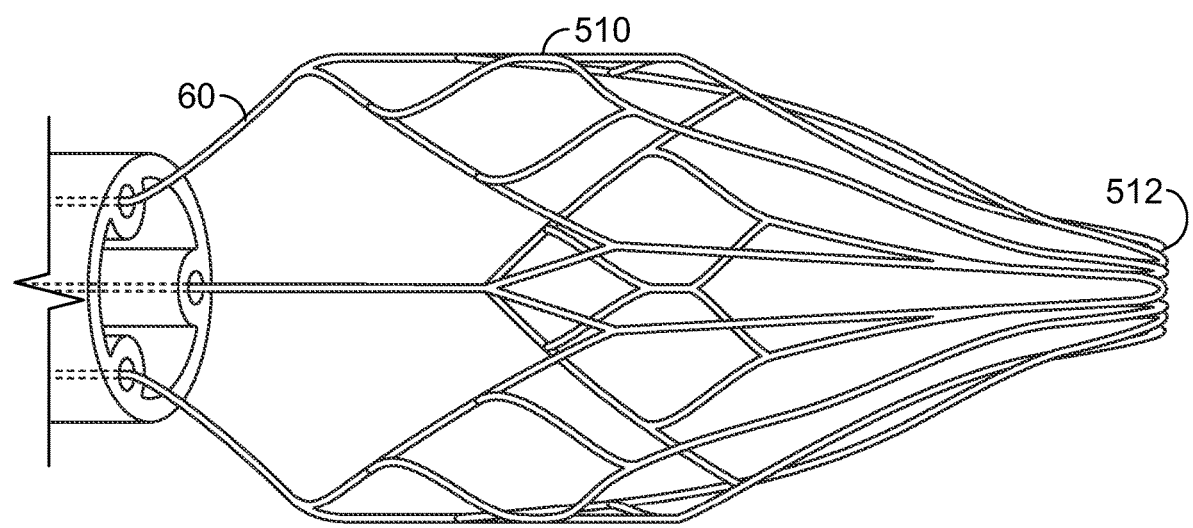
FIG. 18B

MULTI-LUMEN SHEATH CENTRAL VENOUS CATHETER WITH VENA CAVA FILTER APPARATUS AND METHOD OF USING SAME

CROSS-REFERENCE TO RELATED APPLICATIONS

This application claim priority to U.S. Provisional Application Ser. No. 61/668,308, filed Jul. 5, 2012, and is related to co-pending U.S. patent application Ser. No. 12/684,839, filed Jan. 8, 2010, which claims priority to Ser. No. 12/684,839 U.S. patent application Ser. No. 11/849,225, filed Aug. 31, 2007, all herein incorporated by reference in their entireties.

BACKGROUND OF THE INVENTION

The present invention pertains generally to the field of filters for capturing material.

The accepted standard of care for patients with venous thromboembolism (VTE) is anticoagulant therapy. Inferior vena cava (IVC) filters are reserved for those patients who fail anticoagulant therapy, or have a complication or contraindication to anticoagulant therapy. Until the early 1970's, the only method of IVC interruption was surgical, either by clipping, ligation or plication. The first clinical experience of an endoluminally-placed device to interrupt IVC flow was reported by Mobin-Uddin et al. in 1969. However, it was not until the introduction of a stainless steel umbrella-type filter by Greenfield et al. in 1973 that an effective method of endoluminally trapping emboli while simultaneously preserving IVC flow became possible. Indeed, for many years, the Greenfield filter set a benchmark by which newer filters were measured. Early generations of filters were inserted by surgical cut-down and venotomy. Eventually filters were able to be inserted percutaneously: initially through large 24 Fr sheaths, though newer generations of filters are able to be delivered through 6 Fr systems.

Despite the safety and efficacy of modern day filters, systemic anticoagulation remains the primary treatment for VTE. Either unfractionated or low molecular weight heparin followed by three months of oral anticoagulation in patients with proximal deep venous thrombosis (DVT) is approximately 94% effective in preventing pulmonary embolism (PE) or recurrent DVT. The routine placement of IVC filters in addition to anticoagulation in patients with documented DVT was investigated by Decousus et al. in a randomized trial. Decousus H, Leizorovicz A, Parent F, et al. A clinical trial of vena caval filters in the prevention of pulmonary embolism in patients with proximal deep-vein thrombosis. N. Engl. J. Med. 1998; 338:409-415. This study revealed that the use of a permanent filter in addition to heparin therapy significantly decreased the occurrence of PE within the first 12 days compared to those without a filter. However, no effect was observed on either immediate or long-term mortality, and by 2 years, the initial benefit seen in the group of patients with filters was offset by a significant increase in the rate of recurrent DVT.

Despite the efficacy of anticoagulant therapy in the management of VTE, there are certain situations and conditions in which the benefits of anticoagulation are outweighed by the risks of instituting such a therapy. These include contraindications and complications of anticoagulant therapy. In such circumstances, there may be absolute or relative indications for filter insertion Currently, there are eight different types of permanent cava filters that are FDA approved. These include the Bird's Nest filter (Cook Incorporated, Bloomington, Ind.), Vena Tech LGM filter (B. Braun, Bethlehem Pa.), Vena Tech LP (B. Braun), Simon Nitinol filter (Bard, Covington, Ga.), Titanium Greenfield filter (Boston Scientific, Natick Mass.), Over-the-Wire Greenfield filter (Boston Scientific), TrapEase filter (Cordis Corp.) and the Günther Tulip filter (Cook Inc.)

Well-founded concerns over the long-term complications of permanent IVC filters, particularly in younger patients in need of PE prophylaxis with a temporary contraindication to anticoagulation, has led to the development of temporary and retrievable filters. Temporary filters remain attached to an accessible transcutaneous catheter or wire. These have been used primarily in Europe for PE prophylaxis during thrombolytic therapy for DVT. Currently these devices are not approved for use in the United States. Retrievable filters are very similar in appearance to permanent filters, but with modifications to the caval attachment sites and/or hooks at one end that can facilitate their removal. Retrievable filters are currently available in the United States, examples of these include the Günther Tulip (Cook Inc.), Opt Ease (Cordis Corp.), and Recovery nitinol filters (Bard Peripheral Vascular, Tempe, Ariz.) Lin P H, et al., Vena caval filters in the treatment of acute DVT. Endovascular Today 2005; January: 40-50. The time limit of retrievability is in part dependant on the rate of endothelialization of the device, which typically occurs within 2 weeks. However, differences in design may extend the time period in which the filter may be safely retrieved.

Currently no consensus exists as to which patients have an indication for a retrievable filter. However, it is generally accepted that patients at high risk for pulmonary embolism or with documented PE and with a temporary contraindication to anticoagulation are candidates.

Certain circumstances preclude the placement of a filter in the infrarenal IVC. This includes thrombus extending into the infrarenal IVC, renal vein thrombosis or pregnancy. The safety of suprarenal placement of IVC filters is well documented, with no reported instances of renal dysfunction and no differences in the rates of filter migration, recurrent PE or caval thrombosis.

The rate of upper extremity DVT is on the rise. This is predominantly due to an increasing number of patients having short- and long-term upper extremity central venous access catheters. In one study, 88% of patients found to have an upper extremity DVT had a central venous catheter present at the site of thrombosis at the time of diagnosis or within the previous two weeks. Pulmonary embolism may complicate upper extremity DVT in 12-16% of cases. In patients who have such a complication or contraindication to anticoagulation, a filter can be safely placed immediately below the confluence of the brachiocephalic veins. However, misplacement of an SVC filter is theoretically more likely than with an IVC filter because of the relatively short target area for deployment.

The most common imaging modality used for filter insertion is fluoroscopy, performed either in an interventional suite or an operating room. Bedside placement of filters has inherent advantages, particularly for critically ill patients in intensive care settings where transport can be avoided. Portable fluoroscopy, surface duplex ultrasound and intravascular ultrasound (IVUS) have all been used to assist with bedside filter placement.

Vena cava filter placement frequently occurs concomitantly with central access line placement or in critically ill patients that already have a central access line in place. Heretofore, however, there have been no devices which combine the function of a central access catheter and a removable vena cava filter.

SUMMARY OF THE INVENTION

A multi-lumen sheath coupled to a central venous catheter and a filter member is disclosed herewith, which may be useful both as a central venous access catheter for administration of intravenous fluids, bioactive agents, contrast agents, flushing agents, pressurized fluids for mechanical thrombolysis and/or withdrawal of blood samples and for capture of venous thrombus or venous emboli.

In one embodiment, a medical device comprises: a multi-lumen sheath having a central lumen and a thickness surrounding the central lumen, a first port associated with a first lumen within the thickness of the multi-lumen sheath; a second port associated with a second lumen within the thickness of the multi-lumen sheath; and a third port associated with a third lumen within the thickness of the multi-lumen sheath; at least one wire longitudinally disposed within the first lumen, the second lumen, and the third lumen; a filter member operably associated with the distal ends of the at least one wires longitudinally disposed within the first lumen, the second lumen, and third lumen, wherein the at least one wires allow expansion of the filter member to a diametrically enlarged state from a diametrically collapsed state.

In another embodiment, a medical device is disclosed and generally comprises: a multi-lumen sheath having a central lumen and a thickness surrounding the central lumen, a first port associated with a first lumen within the thickness of the multi-lumen sheath; a second port associated with a second lumen within the thickness of the multi-lumen sheath; a third port associated with a third lumen within the thickness of the multi-lumen sheath; and a fourth port associated with a fourth lumen within the thickness of the multi-lumen sheath; at least one wire longitudinally disposed within the first lumen and the second lumen; a filter member operably associated with the distal ends of the at least one wires longitudinally disposed within the first lumen and second lumen, wherein the at least one wires allow expansion of the filter member to a diametrically enlarged state from a diametrically collapsed state.

BRIEF DESCRIPTION OF THE DRAWINGS

FIG. 2A is a partial cross-sectional side view of a multi-lumen sheath in accordance with a first embodiment of the present invention; and FIG. 2B is a side view of a multi-lumen sheath in accordance with another embodiment of the present invention.

FIG. 3A is a cross-sectional view taken along line 3A-3A of FIG. 2A; and FIG. 3B is a cross-sectional view taken along line 3B-3B of FIG. 2B.

FIG. 4A is a cross-sectional view taken along line 4A-4A of FIG. 2A; and FIG. 4B is An end view taken along line 4B-4B of FIG. 2B FIG. 5 is a side view of the multi-lumen wire body in accordance with one embodiment of the present invention.

FIG. 6 is a cross-sectional view taken along line 6-6 of FIG. 5.

FIG. 7 is a cross-sectional view taken along line 7-7 of FIG. 5.

FIG. 8 is a cross-sectional view taken along line 8-8 of FIG. 5.

FIG. 10A is a side view of the multi-lumen outer sheath in accordance with an embodiment of the present invention; FIG. 10B is a cross-sectional view taken along line 10B-10B of FIG. 10A; and FIG. 10C is a cross-sectional view taken along line 10C-10C of FIG. 9A.

FIGS. 12A-12H are cross-sectional views of alternative configurations of the multi-lumen sheath.

FIGS. 18A and 18B are perspective views of an alternative embodiment of a filter member mounted at a distal end of the multi-lumen sheath and deployed with wires disposed therein.

DETAILED DESCRIPTION OF THE PREFERRED EMBODIMENTS

Figure 1:
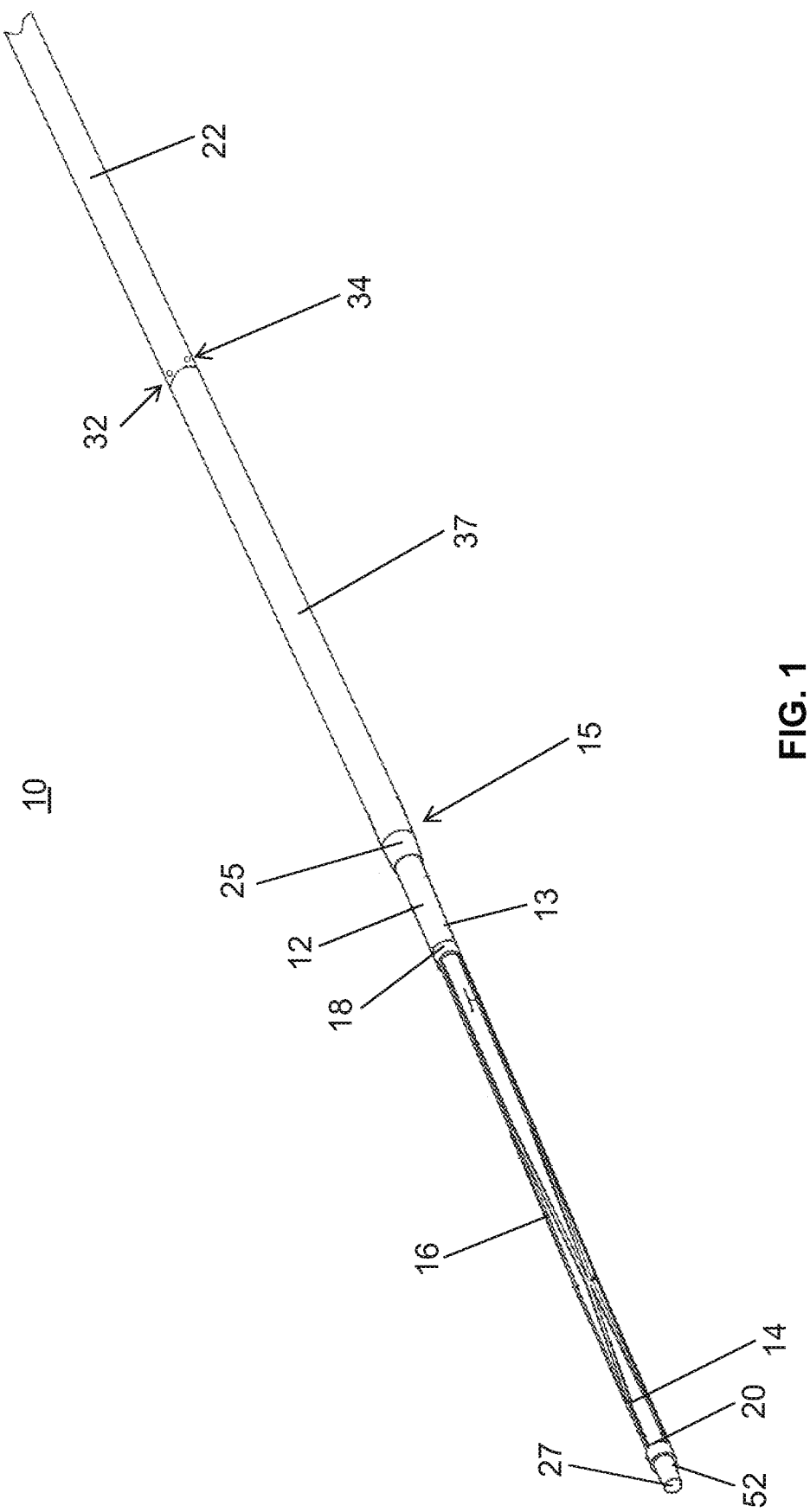
FIG. 1 is a perspective view of a multi-lumen outer sheath in accordance with a first embodiment depicting the filter member in an unexpanded state.

The embodiments disclosed herein may be configured for either a femoral approach or a jugular approach to the inferior vena cava. Vena cava filters are typically deployed infrarenaly, but may also be deployed suprarenaly. It will be understood that within the inferior vena cava blood flow is superior, i.e., toward the patients head. Thus, in all embodiments, the vena cava filter will be positioned so that it opens inferiorly, i.e., away from the patient's head and toward the direction of the blood flow. It will be appreciated, therefore, that in the present invention, the vena cava filter will have a different axial orientation on the central access catheter depending upon whether the device is intended for use in a femoral approach or a jugular approach.

More particularly, the multi-lumen outer sheath and a wire body having a proximal end and a distal end thereof relative to the longitudinal axis of the catheter, a vena cava filter near the distal end of the wire body, at least one of a port proximal the vena cava filter to deliver fluid to a space delimited by the vena cava filter. The multi-lumen sheath includes a central lumen through which the wire body is longitudinally disposed and a filter capsule distally attached to the outer sheath. The filter may be diametrically constrained within the filter capsule and upon longitudinal movement of the wire body or sheath, the filter may diametrically expand by the distal movement of the filter, or the proximal movement of the sheath. The multi-lumen sheath reduces the diameter of the wire body, such that the wire body may be a small diameter similar to a guidewire. The multi-lumen sheath may include a first lumen or a second lumen for disposing thrombolytic agent towards the distal end of the multi-sheath and lyse any clots or thrombus contained within the filter in the diametrically expandable state. Alternatively, the wire body and the filter may be removed from the central lumen of the multi-lumen sheath, such that thrombectomy or embolectromy devices and/or agents may be disposed to lyse thrombus. The central lumen may also include a wire disposed and fixedly attached to the inner surface of the central lumen as to provide additional longitudinal rigidity to facilitate filter retrieval.

In one embodiment, a method capturing thrombus within a blood vessel is disclosed and comprises: introducing a multi-lumen sheath having a wire body operably disposed within a central lumen of the multi-lumen sheath and a filter member operably coupled to the distal end of the wire body; containing the filter member within a filter capsule coaxially coupled to the distal end of the multi-lumen sheath; deploying the filter by longitudinal movement of the wire body, whereby the deployed filter has an enlarged diametric opening infusing a fluid through at least one lumen in the multi-lumen sheath in communication with at least one infusion port passing through the multi-lumen sheath. The method may further comprise the step of introducing a fluid or thrombectomy device through a lumen in the wire body. The method may further comprise introducing a thrombectomy device through the central lumen of the multi-lumen sheath, and infusing a fluid through at least one of a third lumen to lyse thrombus captured within the filter member. The method may further comprise the step of sensing fluid flow velocities within the blood vessel while introducing the multi-lumen catheter within the blood vessel. The method may further comprise sensing a pressure differential across the filter member through a proximal port in the multi-lumen catheter proximal the filter that communicates with a first lumen in the multi-lumen catheter and through a distal port in the multi-lumen catheter distal the filter that communicates with a second lumen in the multi-lumen catheter, said pressure differential being indicative of the extent of thrombus capture within the filter member. The method may further comprise infusing a thrombolytic fluid through the at least one lumen in the multi-lumen catheter that communicates with the at least one infusion port. The method may further comprise infusing a thrombolytic fluid further comprises the step of infusing a thrombolytic agent. The method may further comprise infusing a thrombolytic fluid further comprises the step of infusing a pressurized fluid to mechanically thrombolyse thrombus captured in the filter member or introducing a mechanical wire to mechanically break thrombus captured in the filter member.

In the accompanying Figures like structural or functional elements are designated by like reference numerals, e.g., 16, 116, 216, 316, 416 represent similar structural or functional elements across different embodiments of the invention. With particular reference to FIGS. 1-4, a multi-lumen sheath Central Venous Catheter ("CVC") 10 coupled with an Inferior Vena Cava (IVC) filter that is composed generally of a wire body or catheter 12 coaxially disposed within a multi-lumen sheath 22 and a filter capsule 37 to hold a filter member 16. Alternatively, the filter capsule 37 may be removed and the filter member 16 may be disposed at least one of the lumens of the multi-lumen sheath 22. The multi-lumen sheath 22 includes a central lumen 30 through which the wire body 12 is coaxially disposed and permits longitudinal movement therethrough. Alternatively, the central lumen 30 may be employed for Central Vena Cava (CVC) access, including, but not limited to contrast injection, guidewire passage, infusion, blood withdrawal, thrombectomy device passage, and the like. Alternatively, the central lumen 30 may be included off-axis but still parallel to the longitudinal axis of the multi-lumen sheath 22. The multi-lumen sheath 22 includes a first port 32 associated with a first lumen 44, and a second port 34 associated with a second lumen 42, as shown in FIG. 2A. Preferably, the first port 32 and second port 34 are disposed on the distal end of the multi-lumen sheath; however, the first port and second port may be disposed along any longitudinal portion of the multi-lumen sheath. The disposition of the first port 32 and second port 34 may exit through the side of the multi-lumen sheath, and alternatively, the first port 32 and second port 34 may also terminate at the end of the multi-lumen sheath 22, pointing distally and emitting within the filter capsule portion. Thus emitting within the capsule portion of the sheath. The first lumen 44 and the second lumen 42 may extend along the entire longitudinal length of the multi-lumen sheath 22; alternatively, the first and second lumen 44, 42 may extend along at least a portion of the longitudinal length of the multi-lumen outer sheath 22.

The filter member 16, having a first end 18 and a second end 20, is positioned generally on the distal end of the wire body 12 and is generally concentric relative to the wire body 12, as shown in FIG. 1. Alternatively, the filter member may not be positioned on the wire body 12 and may be free floating filter member 16 that includes a connection point on the distal end 20. The wire body 12 has a proximal section 13 and a distal section 14, which is longitudinally opposite the proximal section 13, and which may have a relatively smaller diametric profile than the proximal section 13.

As used in this application, unless otherwise specifically stated, the terms "proximal" and "distal" are intended to refer to positions relative to the longitudinal axis of the wire body 12. Those skilled in the art will understand that the wire body 12 has a distal end which is first inserted into the patient and a proximal end which opposite the distal end. Additionally, the terms "inferior" or "inferiorly" are intended to refer to the anatomic orientation of being in a direction away from the patient's head while the terms "superior" or "superiorly" are intended to refer to the anatomic orientation of being toward the patient's head.

Preferably, the wire body 12 has a very low profile and a high degree of longitudinal rigidity to maintain CVC functionality as well as to provide responsive force feedback when retrieving the filter. The wire body 12 may include an atraumatic tip 52 or integral floppy tip on the distal section 14, to obviate the need for a guidewire during filter placement, as shown in FIG. 1. The atraumatic tip 52 preferably includes a radio-opaque marker to aid in positional visualization of the distal end of the wire body 12. In an alternative embodiment, the wire body 12 may be hypo-tube or single lumen tube in place of the wire body. If the wire body 12 includes a single-lumen tube, the single lumen may serve as a passage for thrombectomy or embolectomy devices and/or agents to access thrombus captured in the filter while the filter is open to any degree.

The filter capsule 37 is concentrically disposed over the wire body 12 and the filter member 16 such that relative movement of the wire body 12 and the filter member 16 either exposes the filter member 16 or captures the filter member 16 within the filter capsule 37, as shown in FIG. 2A. The filter capsule 36 may be a hypotube that is bonded at the distal end of the multi-lumen sheath 22, generally shown as reference 15. The bonding may be any type of bonding as known in the art. In one embodiment, the filter capsule may have a self-centering aspect, as described in U.S. patent application Ser. No. 13/091,826, filed Apr. 21, 2011, incorporated by reference herein.

In an alternative embodiment, the multi-lumen sheath 22 does not include the wire body 12 to deploy the filter member 16, as shown in FIGS. 2B-4B. In this embodiment, the multi-lumen sheath 22 includes a first port 32 associated with a first lumen 44; a second port 34 associated with a second lumen 42; and a third port 36 associated with a third lumen 40 as shown in FIG. 2A. Preferably, the first port 32, the second port 34, and third port 36 are disposed on the distal end of the multi-lumen sheath 22. The first lumen 44, the second lumen 42, and the third lumen 40 include a thickness thereabout, such as to remain separate from the central lumen 30. The first lumen 44, the second lumen 42, and the third lumen 40 are operably coupled with at least one wire 60 that are longitudinally disposed within the lumens 44, 42, 40 and the at least one wires 60 are operably coupled with the filter member 16. The disposition of the first port 32, the second port 34, and third port 36 may exit through the side of the multi-lumen sheath, and alternatively, the first port 32 and second port 34 may also terminate at the end of the multi-lumen sheath 22, pointing distally and allowing the at least one wire 60 to be expanded distal of the multi-lumen sheath and allow expansion of the filter member 16 to be deployed or diametrically enlarged from a diametrically collapsed state on the distal end of the multi-lumen sheath 22. The first lumen 44, the second lumen 42, and the third lumen 40 may extend along the entire longitudinal length of the multi-lumen sheath 22; alternatively, the first, second, and third lumens 44, 42, 40 may extend along at least a portion of the longitudinal length of the multi-lumen outer sheath 22.

Figure 15A:
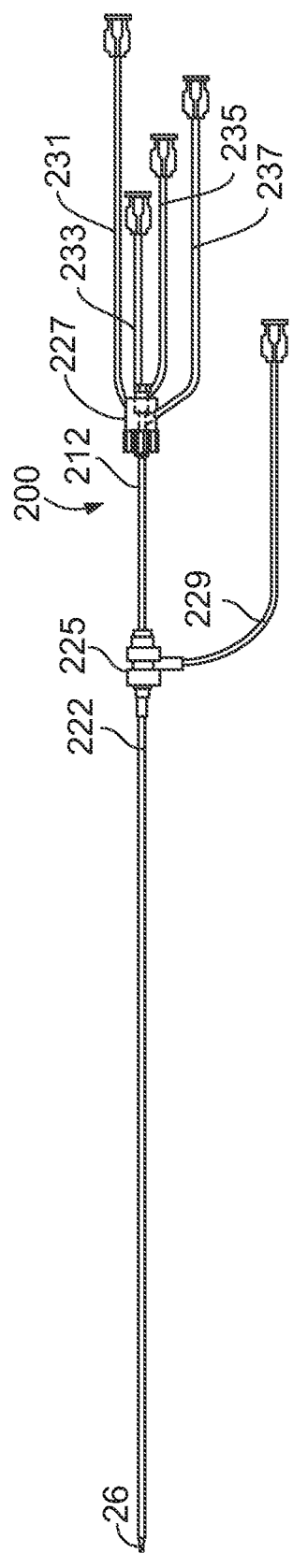
FIG. 15A is a side elevational view of the vena cava central line catheter in its undeployed state.
Figure 15B:
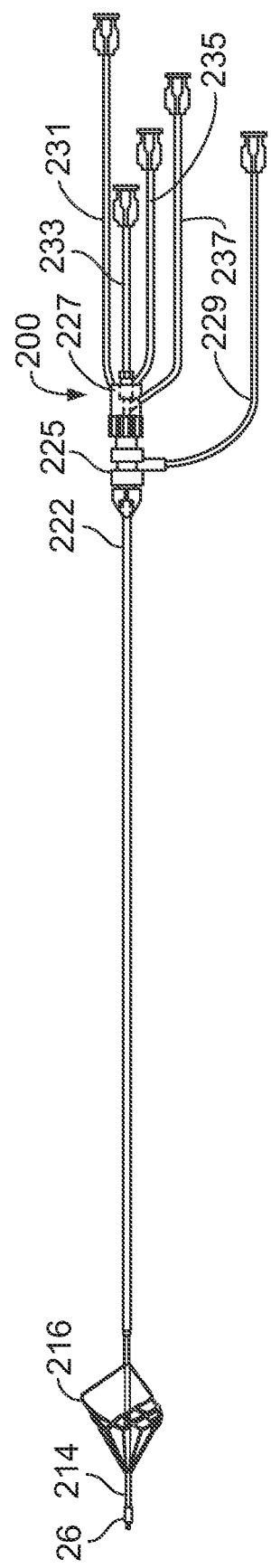
FIG. 15B is a side elevational view of the vena cava central line catheter in its deployed state.

The multi-lumen sheath 22 terminates in an annular opening at a distal end thereof and at first hub member 225 as depicted in FIGS. 15A-15B. The proximal hub 225 will be described more fully hereinafter. The wire body 12 extends through a central bore in the proximal hub 225 and passes through the central lumen 30 of the multi-lumen sheath 22. A second hub member 227, as depicted in FIGS. 15A-15B, is coupled to a proximal end of the wire body 12. The second hub member 227 and the first hub member 225 are removably engageable with each other as will also be described further hereinafter. Alternatively, the hub members may be operable as described in U.S. patent application Ser. No. 13/083,053, filed Apr. 8, 2011 or in U.S. Provisional Application Ser. No. 61/584,716, filed Jan. 9, 2012, each incorporated by reference herein.

An alternative hub member may be deployed on the proximal end of the multi-lumen sheath 22 to deploy the filter member 16 based on wires 60 being longitudinally disposed in the first and second lumens 44, 42, as shown in FIGS. 15C-15K.

Depending upon the orientation of the filter member 16, the first end 18 or the second end 20 may either be fixed or moveable relative to the wire body 12. Alternatively, as will be discussed further hereinafter, the filter member 16 may have only a first end 18 which is fixed to the wire body 12. Alternatively, the first end may be movably coupled with the wire body 12, which permits freedom of rotation of the filter about the wire and some degree of freedom of axial movement between specified axial stops. This would help alleviate rubbing motion between the filter and vena cava wall when the catheter is moved or flexed as the patient moves around.

To facilitate percutaneous introduction of the inventive CVC 10, a physician may employ the multi-lumen sheath as vascular access conduit for the CVC 10. The presence of the filter member 16 at the distal end of the wire body 12 does not decrease the flexibility of the CVC 10, due to the presence of the wire body 12 and/or the filter capsule 37. A physician may deploy and expand the filter member by retracting the multi-lumen outer sheath 22 while holding the filter member in a stationary position. This is sometimes referred to as the "pin and pull" technique in the context of self-expanding stent delivery systems. However, the physician may prefer to push the filter member distally out of the multi-lumen outer sheath. The CVC 10 may be deployed as a central line catheter or as a peripherally inserted central catheter (PICC). A PICC is a form of intravenous access that can be used for a prolonged period of time (e.g. for long chemotherapy regimens, extended antibiotic therapy, or total parenteral nutrition). A PICC is an alternative to subclavian lines, internal jugular lines or femoral lines. A PICC is inserted in a peripheral vein, such as the cephalic vein, basilic vein, or brachial vein and then advanced through increasingly larger veins, toward the heart until the tip rests in the distal superior vena cava or cavoatrial junction. The insertable portion of a PICC varies from 25 to 60 cm in length, that being adequate to reach the desired tip position in most patients. Some lines are designed to be trimmed to the desired length before insertion; others are simply inserted to the needed depth with the excess left outside. As supplied, the line may include a guide wire inside, which is provided to stiffen the (otherwise very flexible) line so it can be threaded through the veins.

The multi-lumen aspect of the multi-lumen outer sheath 22 is shown more clearly in FIGS. 2A-4A. In one embodiment, the multi-lumen outer sheath 22 includes a wire 39 fixedly associated with the wire body 12 or a surface of the central lumen 30. The wire 39 may extend the longitudinal length of the wire body 12 or the central lumen 30 to provide additional support for the filter 16, and decrease the need for a stiff, thick wall multi-lumen sheath. Alternatively, there may be a plurality of wires 39 disposed within the body of the multi-lumen outer sheath 22, as shown in FIG. 3A. The wire body 12 has a proximal section 13 and a distal section 14, which is longitudinally opposite the proximal section 13, and which may have a relatively smaller diametric profile than the proximal section 13. As described above, the first lumen 44 terminates at the proximal port 32, while the second lumen 42 terminates at the distal port 34. The central lumen 30 may be provided that extends the entire longitudinal length of the multi-lumen outer sheath 22 and terminates at the distal end of the multi-lumen outer sheath 22 at a opening 31 that permits the wire body 12 to track along the central lumen 30 during a procedure. The central lumen 30 may also be used to introduce fluids, such as bioactive agents, intravenous fluids or blood transfusions.

Figure 9A:
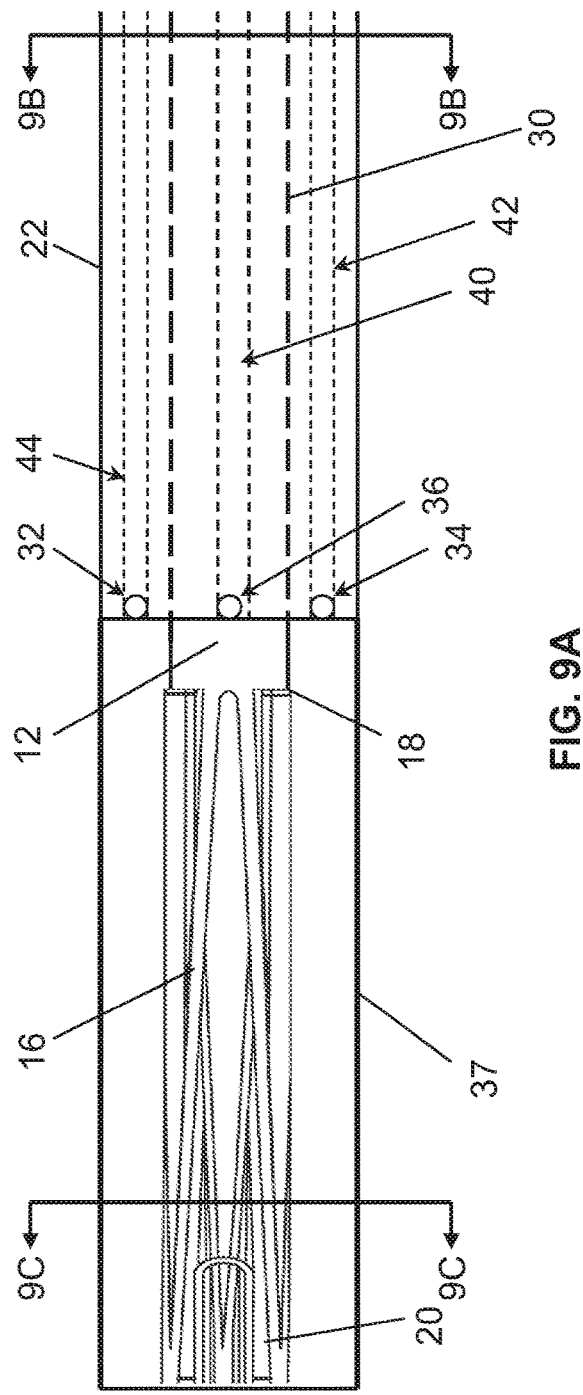
FIG. 9A is a partial cross-sectional side view of the multi-lumen outer sheath in accordance with an alternative embodiment of the present invention.

The multi-lumen aspect of the multi-lumen outer sheath 22 is shown more clearly in FIGS. 2B-4B. In one embodiment, the first, second, and third lumens 44, 42, 40 include a wire 60 longitudinally disposed therein. The first, second, and third lumens 44, 42, 40 may be fixedly associated with the inner surface of the multi-lumen outer sheath 22, such as to form a multi-surfaced central lumen 30. The wires 60 may extend the longitudinal length of the wire multi-lumen outer sheath 22 to expand and contract the filter member 16. Alternatively, there may be any number of wires 60 disposed within the additional lumens of the multi-lumen outer sheath 22, as shown in FIG. 9A. The filter member 16 is expanded when the wires 60 are moved distally from the distal portion of the multi-lumen sheath 22 as to expose the expanded portion of the filter member 16. The expanded filter member 16 has a proximal section and a distal section, whereby the distal section may have a relatively smaller diametric profile than the proximal section. During expansion of the filter member 16, the wires 60 may abut with the outer portion of the first lumen 44, the second lumen 42, and the third lumen 40. The central lumen 30 extends the entire longitudinal length of the multi-lumen outer sheath 22 and terminates at the distal end of the multi-lumen outer sheath 22 at an opening 31 that permits CV access for contrast injection, guidewire passage, infusion, blood withdrawal, thrombectomy device passage, guidewire passage, and the like. The central lumen 30 may also be used to introduce fluids, such as bioactive agents, intravenous fluids or blood transfusions.

Alternatively, as shown in FIGS. 5-8, the wire body 12 may include at least one of a plurality of infusion lumens 54 are provided along the distal section 14, each having at least one infusion port 56 that passes through a wall of the wire body 12, as generally described as the catheter body in U.S. patent application Ser. No. 12/684,839, filed Jan. 8, 2010. The wire body 12 may also include a proximal port 46 associated with a proximal lumen 48 and a distal port 47 associated with a distal lumen 49. Bioactive agents, flushing fluids for flushing or under elevated pressures for mechanical thrombolysis of thrombus in the filter member 16, contrast agents or other fluids may be infused through the infusion lumens and out of the at least one infusion port 56 to pass into the patient's venous system for either local or systemic effect. In accordance with one embodiment of the invention, plural infusion ports 56 are provided with multiple ports 56 being provided in communication with a single infusion lumen 54 and spaced along a longitudinal axis of the wire body 12. Additionally, plural infusion ports 56 may be provided in a circumferentially spaced manner to provide for fluid infusion at points spaced around the circumference of the wire body 12. In this manner, fluid infusion is provided along both the longitudinal axis and the circumferential axis of the wire body 12 within the spatial area defined by and bounded by the filter member 16. Because the plural infusion ports 56 communicate with the spatial area defined by and bounded by filter member 16, fluids introduced through the infusion lumens 54 are directed immediately at thrombus caught within the filter member 16. This permits thrombolytic agents, high pressure mechanical thrombolysis using a pressurized saline flush to be introduced directly to the situs of thrombus capture within filter member 16. Alternatively, thermal, ultrasound or other types of thrombolysis may be employed to disrupt thrombus captured by the filter member 16. For example, the first or second lumen 42, 44 in the multi-lumen outer sheath 22 and the wire body 12 may also be used to introduce a thrombolytic to the filter and shower the filter to disrupt thrombus caught by the filter member 16. Additionally, the balloon depicted in FIGS. 16-17 may be positioned adjacent the filter member 16 and be provided with plural openings oriented in the direction of the filter member 16 to facilitate thrombolysis.

It will be understood, by those skilled in the art, that alternative arrangements of the first lumen 44, the second lumen 42, the central lumen 30, or the infusion lumens 54 are possible and contemplated by the present invention. The number and arrangement of lumens in the wire body 12 is a function of the desired number of operable ports passing through the walls of the wire body 12, the relative position of the operable ports, the desired position and geometry of the central lumen 30, the desired longitudinal flexibility of the wire body 12, the desirable degree of kink resistance of the wire body 12, and other factors which are known to one of ordinary skill in the catheter arts.

While the present invention is not limited to specific dimensional sizes of either the wire body member 12, the multi-lumen outer sheath 22, lumen diameter or port dimension, an exemplary outer diameter size of the outer sheath 22 is between 8 Fr (2.7 mm) and 9 Fr (3.0 mm) while an exemplary outer diameter size of the catheter member 12 is between 6 Fr (2.0 mm) and 7 Fr. A diametric transition taper 15 may be provided between the proximal portion 13 and the distal portion 14 of the wire body 12 corresponding to the thickness of the filter member 16. In this manner, the outer surface of the filter member 16 is substantially co-planar with the outer diameter of the proximal portion 13 of the wire body 12 about its entire circumference. Alternatively, the catheter body member 12 may have a constant diameter and the filter member 16 coupled to an outer surface of the catheter body member 12, with the outer sheath 22 having a luminal diameter sufficient to fit over the filter member 16. Moreover, the fixed first end 18 of filter 16 is positioned adjacent and in abutting relationship with the diametric transition 15, while the moveable second end 20 of filter member 16 is concentrically positioned around the distal section 14 of wire body 12 and is reciprocally moveable thereupon to accommodate diametric expansion of the filter member 16. Lumen diameter and port dimension are a function of design requirements and are variable depending upon the desired purpose and function of the lumen or port, e.g., pressure sensing, infusion, evacuation, guidewire, flow sensing, or flow conduit. Alternatively, the wire body could terminate at the filter attachment location (18) to leave the inside of the filter completely open. And if the wire body is a single lumen tube or hypotube, the luminal passage could be used for high pressure directed saline jet directly into captured thrombus or direct access to the clot with a wire or flagellator to mechanically macerate the trapped thrombus. An example of a flagellator is the Cleaner Rotational Thrombectomy System by Rex Medical, which is an atherectomy system based around a battery powered Cleaner device that rotates a tip at 4,000 RPM for drilling through arterial plaque. (http://medgadget.com/2010/03/rex_medical_cleaner_rotational_thrombectomy_system_wins_us_green_light-.html, incorporated by reference herein.)

In order to aid a physician in visualizing the CVAF 10 in vivo, at least one radio-opaque or other viewable marker may be provided. A first marker 25 is provided at the distal end of the outer sheath 22 and a second marker 27 may be provided at a distal tip of the wire body 12, as shown in FIG. 1. It will be understood that when the outer sheath 22 is in its non-retracted delivery position, that the filter 16 will be covered and the marker 24 and the second marker 27 will be adjacent or in close proximity with one another. Alternatively, the outer sheath 22 may, itself, be made of or include a radio-opaque or other viewable material, such as a metal braid or metal reinforcement within or applied to a polymeric sheath. The first and second markers 24, 27 or the material of the outer sheath 22 may enhance visualization of the CVC 10 under fluoroscopy, ultrasound or other visualization or guidance technique.

Figure 9B:
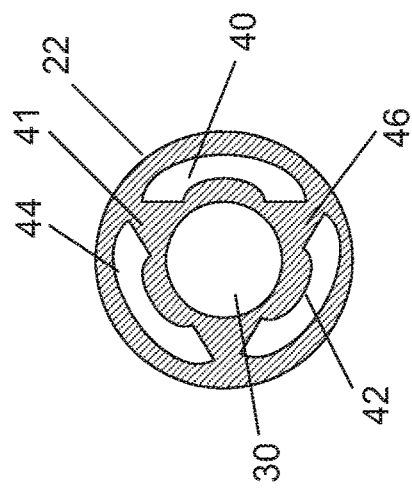
FIG. 9B is a cross-sectional view taken along line 9B-9B of FIG. 9A.
Figure 9C:
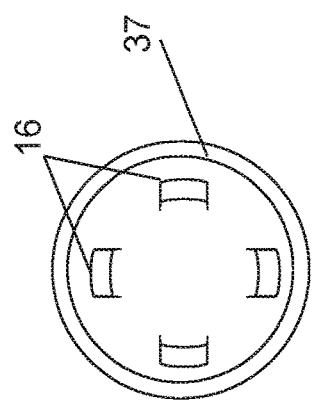
FIG. 9C is a cross-sectional view taken along line 9C-9C of FIG. 9A.

FIGS. 9A-9C illustrate a second embodiment of the CVC 50. Unlike CVC 10, CVC 50 includes a third lumen 40 within the multi-lumen sheath 22. Rather, while the general construct of CVC 50 is similar to that of CVC 10, a different configuration of the inner lumens is employed. CVC 50, like CVC 10, consists generally of a multi-lumen sheath 22 having a first port 32 associated with a first lumen 44, a second port 34 associated with a second lumen 42. However, unlike CVC 10, the multi-lumen sheath 22 includes a third port 36 associate with a third lumen 40, and the filter member 16, having a fixed first end 18 and an expandable second end 20 that is not attached to the wire body 12, as shown in FIG. 9C. The wire body 12 has a proximal section 13 and distal section 14, which is longitudinally opposite the proximal section 13 which may have a relatively smaller diametric profile than the proximal section 13. As described above, the first lumen 44 terminates at the first port 32, while the second lumen 42 terminates at the second port 34 along the distal end of the multi-lumen sheath 22. Bioactive agents, flushing fluids, pressurized mechanical thrombolytic fluids, or other fluids may be infused through the lumens 40, 42, 44 and out of the at least one port 32, 34, 36 to pass into the space defined by the filter member 16 and ultimately into the patient's venous system for either local or systemic effect.

FIGS. 10A-10C illustrate another embodiment of the multi-lumen sheath 22. Unlike CVC 10, the multi-lumen sheath 22 includes a fourth lumen 45 traversing the longitudinal length of the multi-lumen sheath 22 and a fourth port 35 on the distal end of the fourth lumen 45 of the multi-lumen sheath 22. The distal end 20 of the filter member 16 is shown in FIG. 10C, which includes a common connection point on the distal end 20 of the filter member 16. While the general construct of multi-lumen sheath 22 is similar to that of CVC 10, a different configuration of the inner lumens is employed. The multi-lumen sheath 22 includes a first port 32 associated with a first lumen 44, a second port 34 associated with a second lumen 42, and a third port 36 associated with a third lumen 40, as shown in FIG. 10A. At least one wire 60 extends from and is operably associated with the first and second lumens 44, 42 and operably engages the filter member 16. However, unlike previous multi-lumen sheaths 22, the third and fourth lumens 40 and 45 do not include a wire 60 disposed therein, but rather are operably coupled to infusion sources or aspiration sources. The third and fourth lumens 40 and 45 may operate as infusion jets to propel saline towards to the filter member 16 or operate as aspiration sources to suck fluid or clots stuck in the filter member. Alternatively, the central lumen 30 may be used for thrombus aspiration depending on the size of the thrombus.

Figure 11A:
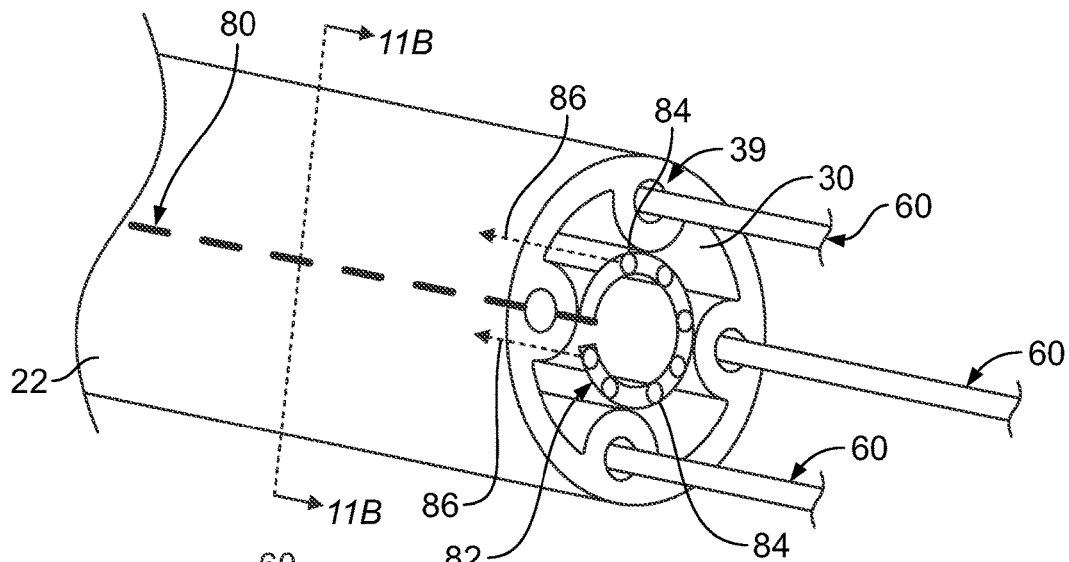
FIG. 11A is a perspective view of one embodiment of the multi-lumen sheath with a central tubing line.
Figure 11B:
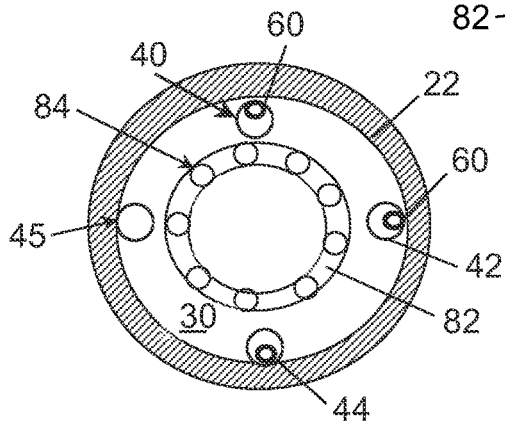
FIG. 11B is a cross-sectional view taken along line 11B-11B of FIG. 11A.
Figure 11C:
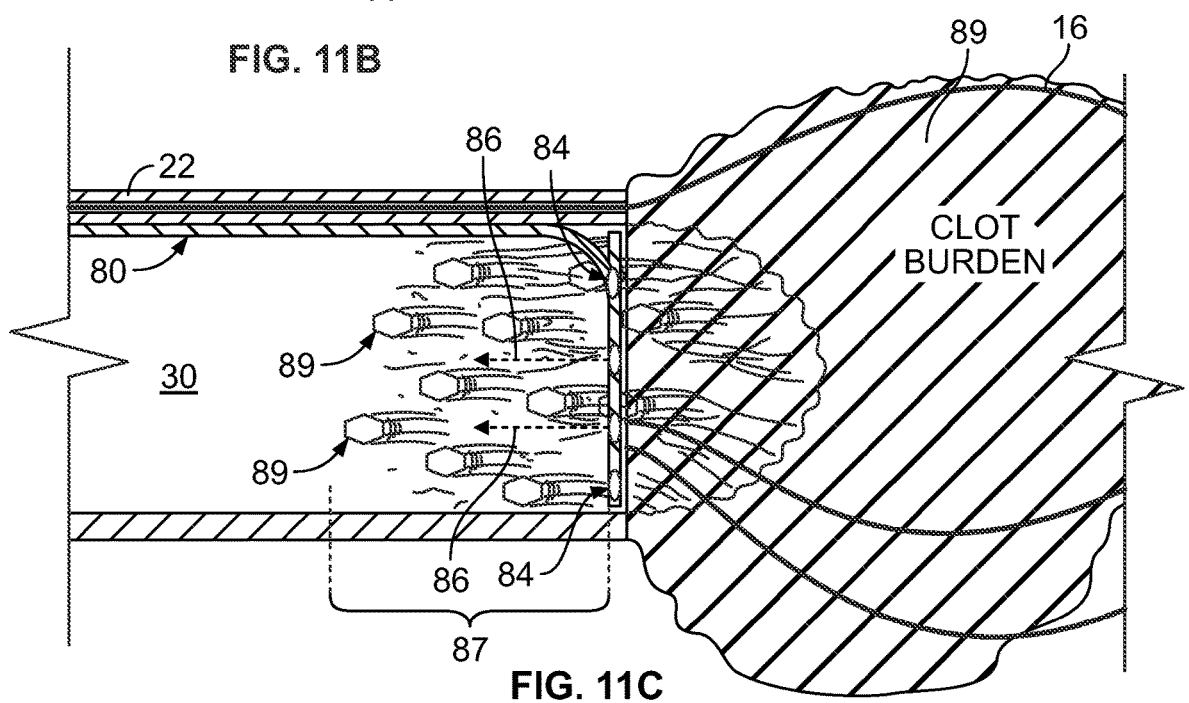
FIG. 11C is side view of the multi-lumen sheath with the central tubing line and illustrating a clot burden within the filter member being aspirated proximally within the central lumen.

FIGS. 11a-11c show an alternative embodiment of the multi-lumen catheter 22 operably coupled with a central tubing line 80 disposed within the central lumen 30 of the multi-lumen sheath 22. The central tubing line 80 provides a conduit through the length of the multi-lumen sheath 22 and includes a closed ring 82 on the distal end of the central tubing line 80. Alternatively, the central tubing line may be an integral lumen within the multi-lumen sheath 22. The closed ring 82 includes a plurality of holes 84 pointing proximally from the distal end of the multi-lumen sheath 22, as to discharge fluid proximally from the distal end of the multi-lumen sheath, generally shown by arrow 86 in FIGS. 11a and 11e. Alternatively, additional closed rings 82 may be provided on the distal end of the central tubing line and may be alternative structures, such as elliptical, polygonal, and the like. In one embodiment, the closed ring 82 may be advanced past the distal end of the multi-lumen sheath 22 and/or be retracted within the central lumen 30 of the multi-lumen sheath 22. In another embodiment, the closed ring 82 may be integrated into the wires 60 and be designed to advance or retract within the wires 60. Alternatively, the closed ring 82 may be replaced with the screw conveyor system to displace fluid proximally from the distal end of the multi-lumen sheath 22. Upon exiting the plurality of holes 84, the high pressure liquid would reduce pressure within the central lumen 30 by increasing velocity of the fluid proximal from the distal end of the multi-lumen sheath, thus producing a suction zone 87 within the closed ring 82 and proximal from the closed ring 82 by nature of the Bernoulli Venturi effect, as shown in FIG. 11c. This suction zone 87 at the distal tip of the multi-lumen sheath 22 could then be employed to aspirate thrombus or clot 89 from within the filter member 16 into the central lumen 30 as the filter member 16 is retrieved into the collapsed or contracted state. Additional suction for aspiration may be applied to the central lumen 30 of the multi-lumen sheath 22 to provide for an integral rheolytic thrombus aspiration. The multiple wires 60 of the filter may have dedicated lumens 40, 42, 44, and 45, and thus the central lumen 30 would be unobstructed through-out the length of the multi-lumen sheath 22.

As shown in FIGS. 6-8, the lumens 40, 42, 44 are bounded by and separated from each other by first catheter septum 41 and second catheter septum 46 which also aid in providing structural support for the wire body 12. First catheter septum 41 is a generally diametrically and longitudinally extending member that divides the first lumen 44 from the second lumen 42 along the longitudinal axis of the wire body 12. Second catheter septum 46 may comprise a generally U-shaped member that intersects the first catheter septum 41 at a lower aspect of the septum and is connected with an inner wall surface of the wire body 12 at upper aspects of the septum 41.

Figure 12F:
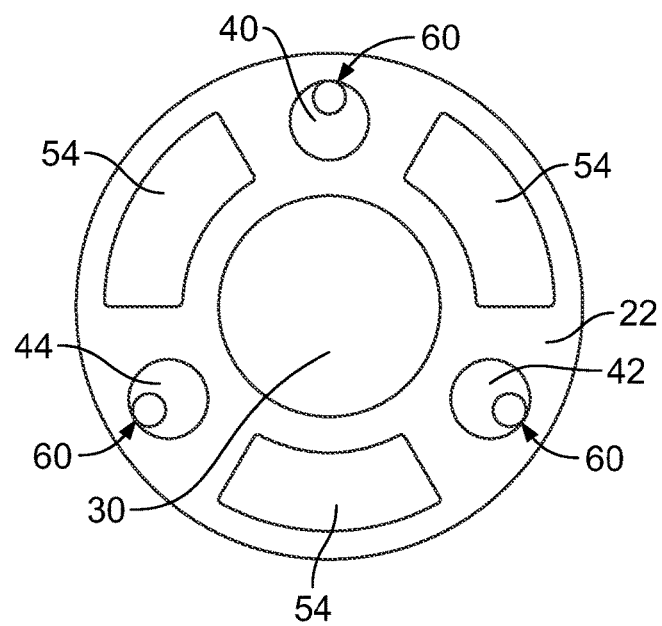

Alternative configurations and arrangements for the multi-lumen sheath 22 and the wire body 12 are shown in FIGS. 12a-12h. FIG. 12a shows an embodiment of the multi-lumen sheath 22 including the first lumen 44, the second lumen 42, and the third lumen 40, wherein the central lumen 30 is concentrically disposed within the multi-lumen sheath 22. The first lumen 42 may include a diameter Df, while the central lumen 30 may include a diameter Dc. In this embodiment, the diameter Dc is less than the diameter Df of the first lumen 34. Cross-sectional areas of the multi-lumen sheath 22 may be targeted to provide adequate mechanical strength for delivering, deploying, or retrieving the filter attached the wire body 22 disposed within the central lumen 30. The diameter Df of the first lumen 42 may be equal to the diameters of the second lumen 42 and the third lumen 40, and the larger diameter lumens 40, 42, 44 allow for high flow rates. However, since the larger lumen 40, 42, 44 take up more of the cross-sectional area of the multi-lumen sheath 22, the lumens 40, 42, 44 may be reinforced with a plurality of longitudinal wires 39 that are fixedly engaged with the inner surface of the lumens 40, 42, 44 and provide appropriate column strength for delivery, deployment, and retrieval of the filter with the filter is coaxially disposed within the filter capsule 37. Guidewire pathway may require rapid exchange design on the distal end of the wire body 12 or may be within the lumen of the wire body 12.

FIG. 12b shows an embodiment of the multi-lumen sheath 22 including the central lumen 30 and the first lumen 42, whereby the central lumen 30 includes a tubing 59 disposed around central lumen 30. The tubing 59 around the central lumen 30 and disposed within the multi-lumen sheath may be off-axis or disposed towards one-side of the longitudinal axis of the multi-lumen sheath 22. In one embodiment, the tubing 59 may be metal, alternatively, the tubing 59 may be polymer, Polyether block amide (Pebax®), and the like. The tubing 59 may provide additional mechanical strength for delivering, deploying, or retrieving the filter. The first lumen 44 may be disposed on the opposite side of the longitudinal axis from the metal tube 59 and the central lumen 30, and the first lumen 44 may include longitudinal tubing 44a for additional mechanical strength and flexibility. The first lumen 44 may include a diameter Df in a conical or elliptical cross-section that is less than the diameter Dc of the central lumen Dc. The multi-lumen sheath 22 may be reinforced with a plurality of longitudinal wires 39 that are disposed within the cross-sectional area of the multi-lumen sheath to provide appropriate column strength for delivery, deployment, and retrieval. Additionally, the longitudinal tubing 44a may include a thickness that is less than a thickness of the tubing 59. FIG. 12c shows a similar embodiment of FIG. 12b, however, the thickness of the longitudinal tubing 44a is greater than the thickness of the tubing 59.

FIG. 12d shows an embodiment of the multi-lumen sheath 22 where the central lumen 30 includes the tubing 59 around the central lumen 30 for additional mechanical support; however, as opposed to FIGS. 12c-d, the central tubing 59 and the central lumen is coaxially disposed within the center of the longitudinal axis of the multi-lumen sheath 22 and the first lumen 44 is coaxially disposed around the central tubing 59 and the central lumen 30. The tubing 59 may include a thickness to support mechanical flexibility.

FIG. 12e shows an embodiment of the multi-lumen sheath 22 where the central lumen 30 and the first lumen 44 are coaxially disposed within the tubing 59. The central lumen 30 includes a diameter Dc that is greater than the diameter Df of the first lumen 44. Coaxially surrounding the tubing 59 is the second lumen 42.

FIG. 12f shows an embodiment of the multi-lumen sheath 22 including the first, second, and third lumens 44, 42, and 40 disposed within the thickness of the multi-lumen sheath 22 and around the central lumen 30, whereby the first, second, and third lumen 44, 42, and 40 are being used for the wires 60 to deploy the filter member 16. At least one infusion lumen 54 is disposed in the thickness of the multi-lumen sheath 22 between the first lumen 44 and second lumen 42, at least one infusion lumen 54 is disposed in the thickness of the multi-lumen sheath 22 and between the second lumen 42 and the third lumen 40, and at least one infusion lumen 54 is disposed in the thickness of the multi-lumen sheath 22 and between the third lumen 40 and the first lumen 44. The infusion lumens 54 include a diameter that is greater than the diameter of the first, second, and third lumens to allow a greater amount of fluid to be disposed from the distal end of the multi-lumen sheath 22.

Figure 12G:
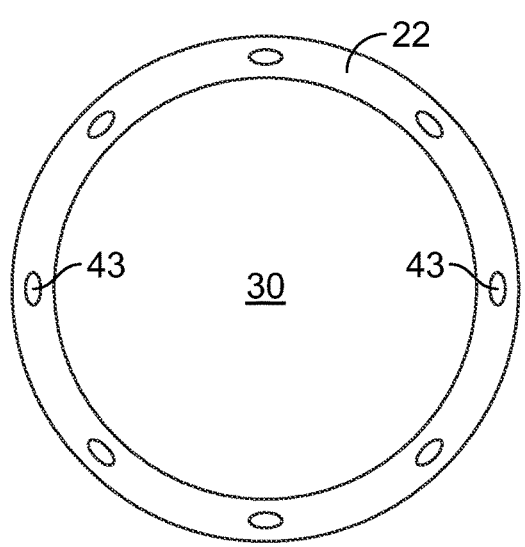

FIG. 12g shows an embodiment of the multi-lumen sheath 22 where a plurality of lumens 43 are disposed within the thickness of the multi-lumen sheath 22 and around the central lumen 30. Although eight lumens 43 are shown in FIG. 12g, any number of lumens 43 may be disposed within the thickness of the multi-lumen sheath 22, such as between 4-8 lumens, or between 5-10 lumens, or between 6-20 lumens.

Figure 12H:
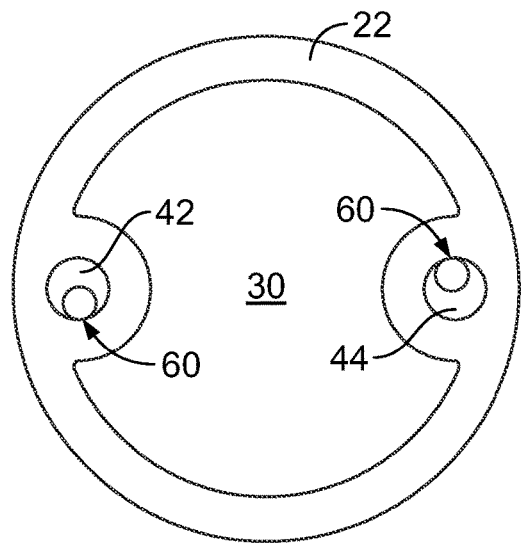

FIG. 12h shows an embodiment of the multi-lumen sheath 22 where the first and second lumens 44, 42 are disposed within the thickness of the multi-lumen sheath 22 and around the central lumen 30. The first, second lumens 44, 42, are being used for the wires 60 to deploy the filter member 16.

Figure 13:
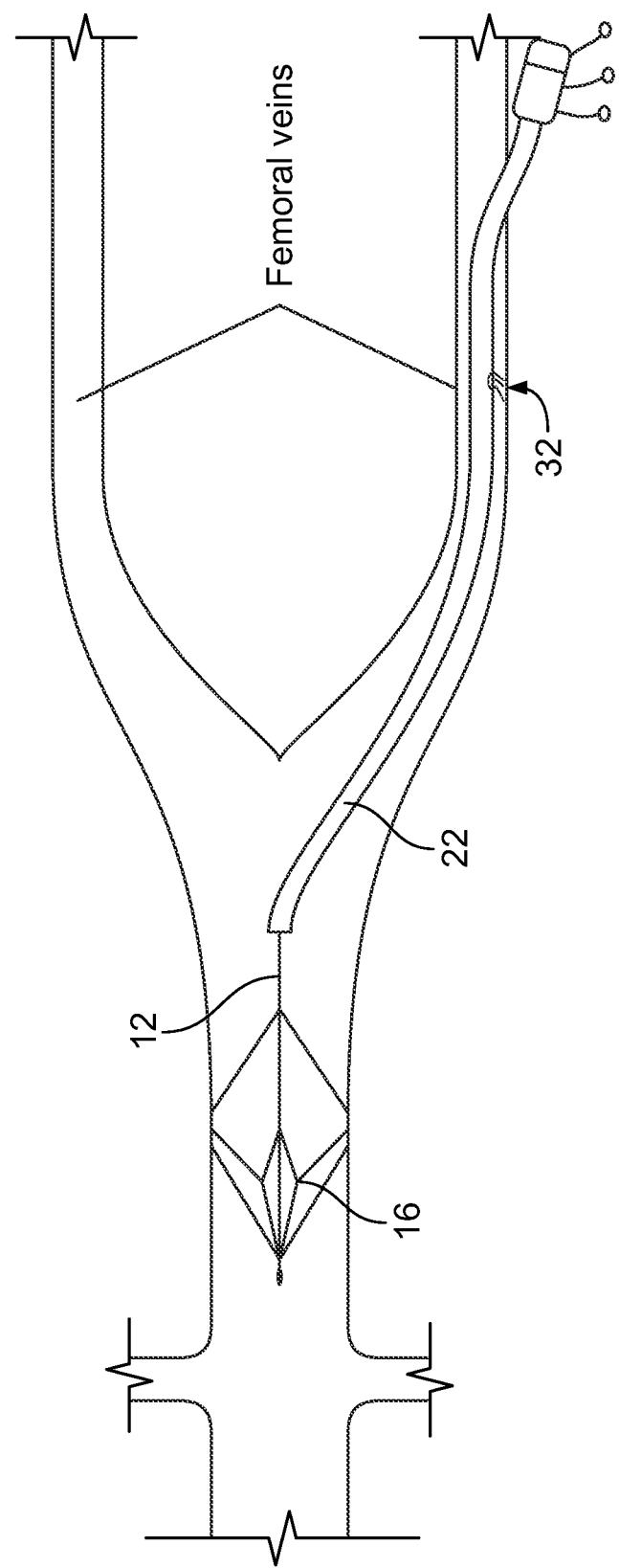
FIG. 13 is a side view of the multi-lumen sheath placed in the femoral vein.

FIG. 13 shows where the first port 32 may be disposed along different longitudinal portions of the multi-lumen sheath 22. In this embodiment, the first port 32 is disposed along the middle length of multi-lumen sheath 22, such that when the multi-lumen sheath 22 is placed in the femoral vein, it allows direct injection of a fluid, contrast agent, medication, or thrombolytic agent proximal to the filter 16 being deployed. Alternatively, the first port 32 could be a single opening or a plurality of openings depending on the function. The plurality of openings is positioned along the longitudinal length of the multi-lumen sheath to facilitate the delivery of therapeutic agents to prevent/reduce catheter related thrombosis.

The filter member 16 has two general configurations. A first configuration consists generally of two opposing generally open conical sections formed by plural interconnected structural elements defining the lateral surfaces of each open conical section, wherein the two opposing generally open conical sections each have open bases facing each other which are interconnected by a generally cylindrical section of the filter member 16. Each open conical section has an open base and an apex, wherein the apices project in opposing directions, with one apex projecting proximally and another apex projecting distally relative to the axis of the catheter. The plural interconnected structural elements forming the lateral surfaces of each generally open conical sections may be strut-like structural members extending generally axially along the longitudinal axis of the filter member 16. The axially extending strut-like structural members may be linear members or may be curved members. The apices of each of the generally open conical sections are formed either of a generally cylindrical collar that serves to couple the filter member 16 to the wire body 12. The generally cylindrical collar is concentrically engaged about the wire body 12 and may be axially movable thereupon, or is formed by connections between adjacent pairs of longitudinal strut-like structural members which circumscribe a circumference of the wire body 12. The generally cylindrical section of the filter member 16 is formed by a generally open lattice of interconnected structural elements which connect the base of a first open conical section to the base of a second open conical section. The generally cylindrical section of the filter member 16 lies in apposition with a vascular wall upon deployment of the filter member 16 with a vascular lumen.

A second general configuration of the filter member 16 consists generally of a single generally open conical section in which a plurality of longitudinal strut-like structural members form the lateral surfaces of the conical section and are connected to a generally cylindrical collar which couples the filter member 16 to the wire body 12 at an apex of the generally open conical section. The base of the generally open conical section is formed by opposing ends of the longitudinal strut-like structural members. A generally cylindrical section of the filter member 16, formed of a generally open lattice of interconnected structural elements, extends from the longitudinal strut-like structural members forming the base of the generally open conical section, to provide a region of the filter member 16 which is in apposition to the vascular wall upon deployment of the filter member.

Figure 14:
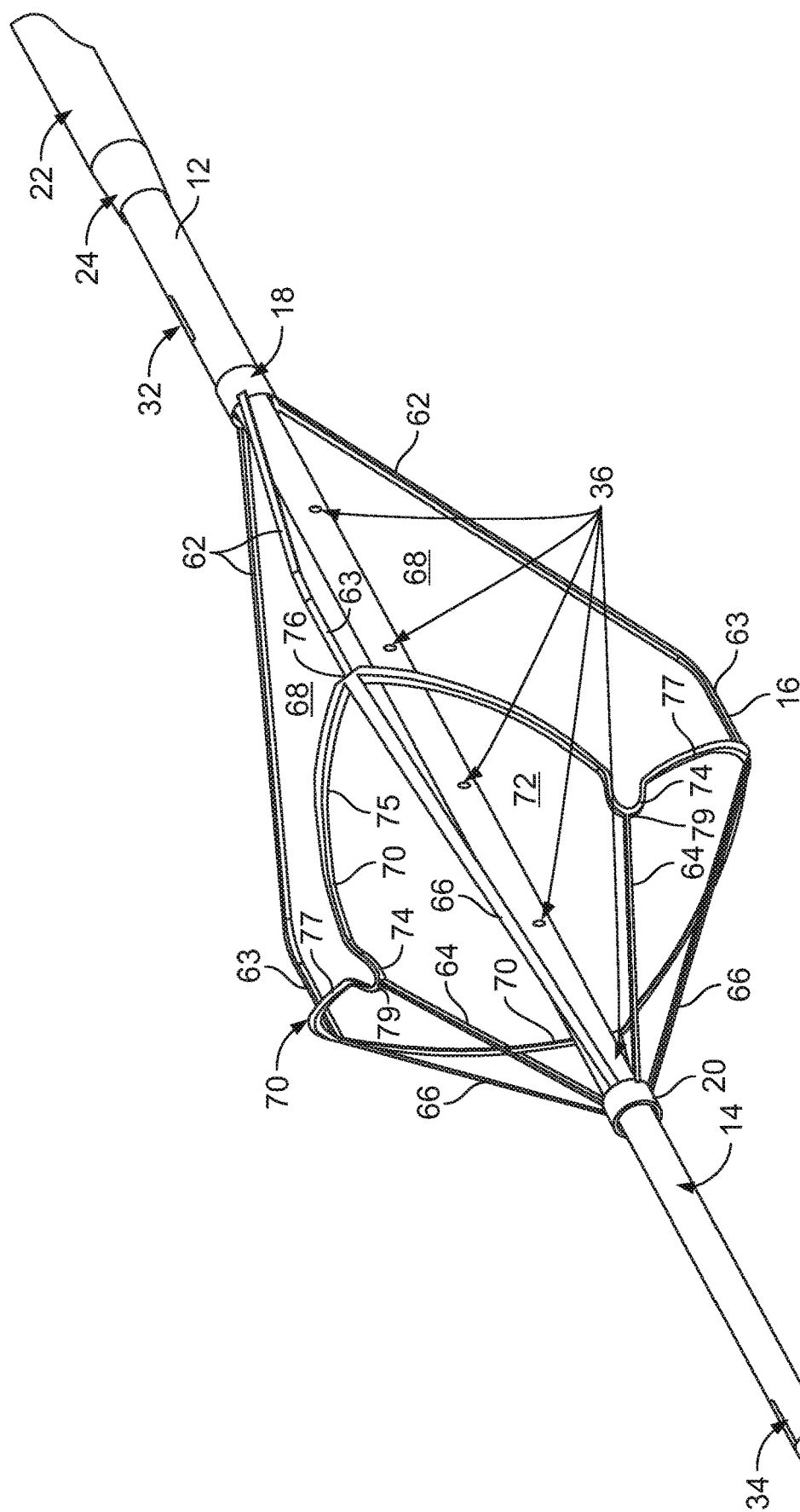
FIG. 14 is a perspective view of the filter member of FIG. 1 illustrating an exemplary embodiment of a vena cava filter according to the present invention in a diametrically expanded state.
Figure 15C:
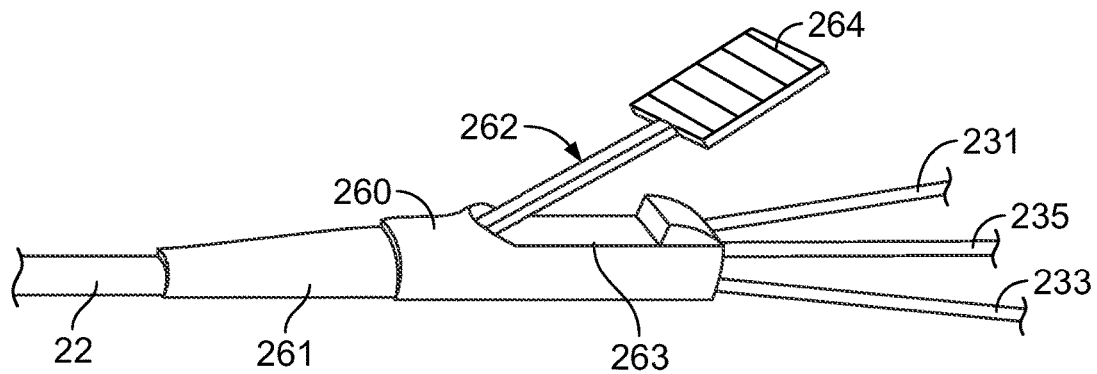
FIGS. 15C-15K are side views of alternative embodiments of the proximal hub member to deploy the filter member by way of wires disposed within the multi-lumen sheath.
Figure 15D:
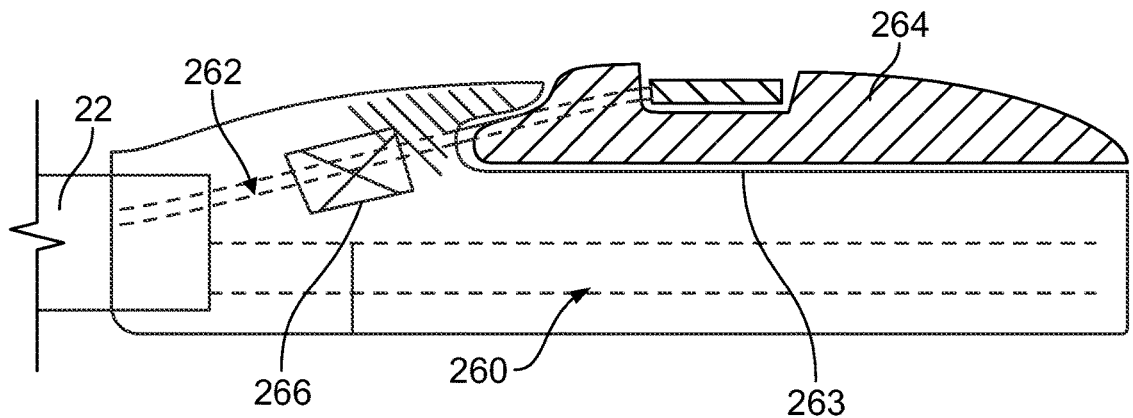

One embodiment of the filter member 16 is illustrated in its diametrically expanded configuration in FIGS. 14-15D.

In this embodiment, filter member 16 consists generally of a first end 18 and a second end 20, each of which consists generally of a tubular structure which is circumferentially positioned about a section of the wire body 12. One of the first end 18 and second end 20 are fixedly coupled to the wire body 12, while the other is movable relative to the wire body 12. At least one of a plurality of first strut members 62, are coupled at their first end to the first end 18 of filter member 16 and each extends axially relative to the longitudinal axis of the wire body 12. Each of the first strut members 62 is an elongate member that, upon diametric expansion of the filter member 16, flares away from the central longitudinal axis of the wire body 12, in a generally tapered conical manner, and terminates in an end section 63 that bends generally parallel to and along the longitudinal axis of the wire body 12. A plurality of second strut members 64 are coupled at an end to the second end 20 of filter member 16 and each extends parallel relative to the longitudinal axis of the wire body 12. A plurality of third strut members 66 are coupled at ends thereof to the an end of the filter member and each extends parallel relative to the longitudinal axis of the wire body 12. It will be appreciated, by those skilled in the art, that the number of struts employed as the first strut members 62, the second strut members 64 and the third strut members 66 forming the filter member 16 may be evenly distributed about a 360 degree circumference and define the lateral wall surfaces of the filter member 16. A circumferential member 70 extends circumferentially to define a circumferential axis of the filter member 16 and has a series of continuous undulations defining peaks a series of peaks 75 and valleys 77 about the circumference of filter member 16. Each of the plurality of first strut members 62, the plurality of second strut members 64 and the plurality of third strut members 66 are coupled to the circumferential member 70 at different points about its circumferential axis and intermediate the proximal end 18 and the distal end 20 of the filter member 16. In its unexpanded state the filter member 16 has a generally tubular shape, while in its expanded state the filter member 16 assumes one of the general configurations discussed above, i.e., either oppositely extending generally open conical sections or a single generally open conical section.

As shown in FIG. 14, the plurality of first strut members 62 are preferably offset from each other by approximately 120 degrees about the circumference of the wire body 12. The plurality of second strut members 64 are also preferably offset from each other by approximately 120 degrees. Finally, the plurality of third strut members 66 are also preferably offset from each other by approximately 120 degrees. Each of the plurality of first strut members 62 couple at a junction 76 to the circumferential member 70 at a peak thereof. Similarly, each of the plurality of third strut members 66 couple at junction 76 to the circumferential member 70 at a peak thereof. In this manner, a first strut member 62 and a third strut member 66 are each coupled to circumferential member 70 at junction 76 and, in this relationship, form a generally linear member that extends along the longitudinal axis of the catheter body and connects between the proximal end 18 of the filter member 16 and the distal end 20 of the filter member 16. Each of the second strut members 64 couple, at their proximal ends to a valley 77 of the circumferential member 70 and connects at a junction 79. Unlike the connections at junction 76 between the plurality of first strut members 62 and the plurality of second strut members, in this embodiment of the filter member 16, there is no member that connects to junction 79 and extends from the first end 18 of the filter member 16. In this configuration, the circumferential member 70 assumes a generally circumferential tri-leaflet ring having three peaks 75 and three valleys 77 which circumferentially circumscribe a central opening 72 which faces inferiorly relative to the patient's blood flow such that the blood flow first passes into the central opening 72 and past the third strut members 66 and the second strut members 64 then past the first strut members 62.

To facilitate bending and folding of the circumferential member 70 between the expanded and unexpanded states, generally U-shaped hinge members 74 may be provided at each of the valleys 77 of the circumferential member 70. It will be understood that each of the plurality of first strut members 62, plurality of second strut members 64, plurality of third strut members 66 and the circumferential member 70 are preferably fabricated of biocompatible materials, such as shape memory alloys, superelastic materials or elastic materials, including, without limitation, titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, cobalt-chromium-molybdenum alloys, nitinol, and stainless steel.

In accordance with a first embodiment of the filter member 16, the filter member consists only of the strut members arrayed to define interstitial openings between the strut members, it being understood that any thrombus captured by the filter member 16 is captured directly by the strut members of the filter member and retained within the space defined within the filter member or by adherence to one or more strut members. In this first embodiment of the filter member 16, no covering of any type is employed on or associated with the filter member 16 to alter or otherwise modify the opening size of the interstitial openings and increase the degree of occlusion of the inferior vena cava. In accordance with a second embodiment of the filter member 16, however, a covering [not shown] having plural openings passing through the covering is employed, preferably on the more distal aspect of the filter member and associated with the strut members to provide at least partial occlusion of the inferior vena cava and expose the blood flow through the inferior vena cava and filter member to a finer or smaller set of openings to capture smaller dimensioned venous thrombus or venous emboli. Such coverings may be made of polymeric materials, woven polymeric materials, woven metal materials, or metallic materials, as is well known in the art.

As depicted in FIGS. 15A-15B, which depict the undeployed state (FIG. 15A) and the deployed state (FIG. 15B) multilumen outer sheath 222 having a plurality of extension lines (231, 233, 235) attached to the sheath side of the hub (225). An inner wire body 214 carries the vena cava filter 216 at a distal end thereof. The inner wire body 214 is concentrically and reciprocally engaged within an outer sheath 222 such that relative axial movement of the inner wire body 214 and the outer sheath 222 either exposes the vena cava filter 216 for deployment or captures the vena cava filter 216 for retrieval. A first hub member 225 is coupled to a proximal end of the outer sheath 222 and a second hub member 227 is coupled to a proximal end of the inner wire body 214. First hub member 225 and second hub member 227 are engageable, such as by a threaded, bayonet, snap fit, friction fit or interference fit fitting, to secure the inner wire body 214 within the outer sheath 222 and restrict relative axial movement of the two elements after deployment of the vena cava filter 216. A flush line 229 communicates with the first hub member 225 and is in fluid communication with a luminal space within the outer sheath 222. A plurality of fluid lines 231, 233, 235 communicate with the second hub member 227 and are each in fluid communication with one of the plural lumens within the multi-lumen outer sheath 222, e.g., lumens communicating with the proximal, distal or infusion ports (not shown). A distal tip 26 is provided at a distal end of the inner catheter.

A jugular approach necessitates that the catheter be introduced retrograde relative to the vector of blood flow within the vena cava, i.e., the catheter is introduced through the jugular vein and directed inferiorly toward an infrarenal position. Additionally, since the blood flow opposes the distal end of the catheter and passes toward the proximal end, the vena cava filter must open inferiorly such that its largest diametric section in apposition to the vessel walls opens toward the distal end of the catheter rather than toward the proximal end of the catheter as with the femoral approach. It will be appreciated by those skilled in the art that in all embodiments of the described central venous access filter, the filter member has a relatively larger opening that is open inferiorly in a direction that opposes the blood flow vector and employs structural elements that taper superiorly along the direction of the blood flow vector to reduce the open surface area of the filter member and capture thrombus.

Figure 15E:
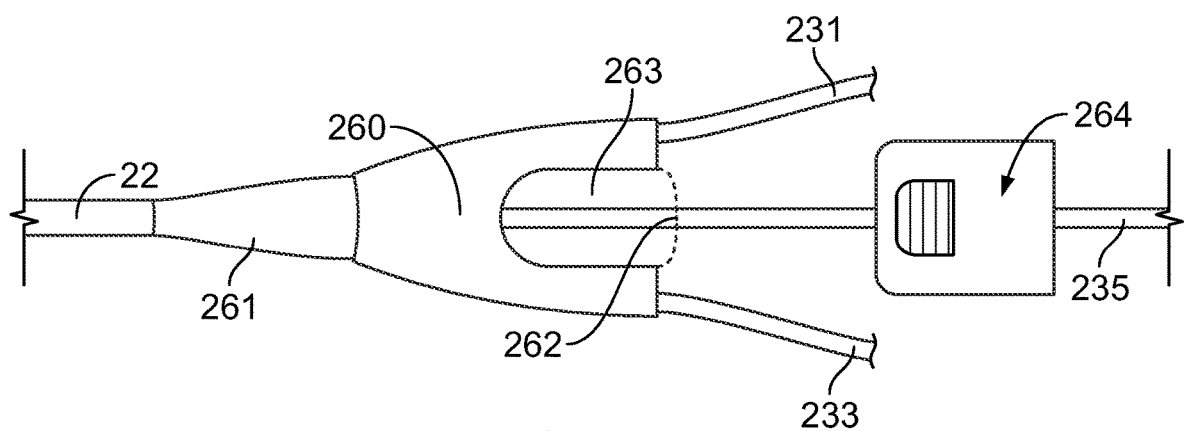

An alternative embodiment of the proximal hub member to deploy the wire 60 based filter member 16 is shown in FIG. 15C, where the proximal end of the multi-lumen sheath 22 is operably coupled to a proximal hub member 260 that includes a top access wire 262 operably coupled with a pull tab 264. The wires 60 are operably coupled with the top access wire 262, and the wires 60 are moved distally by distal movement of the pull tab 264, which is inserted into a depressed section 263 of the proximal hub member 260 to lock the wires 60 in the deployed position for the filter member, as shown in FIG. 15D. In one embodiment, a hemostasis seal 266 is operably coupled with the top access wire 262 to prevent any fluid flowback through the lumens of the wires 60. In one embodiment, the multi-lumen sheath 22 may be operably coupled to a strain relief portion on the proximal end and the proximal hub member 260. In another embodiment, the proximal hub member 260 may include Y-shaped depression section 263, as shown in FIG. 15E, whereby the pull tab 264 operably engages the Y-shaped depression section 263 as to lock the wires 60 and the filter member 16 in the expanded state. The proximal hub member 260 is operably coupled to the plurality of extension lines (231, 233, 235).

Figure 15F:
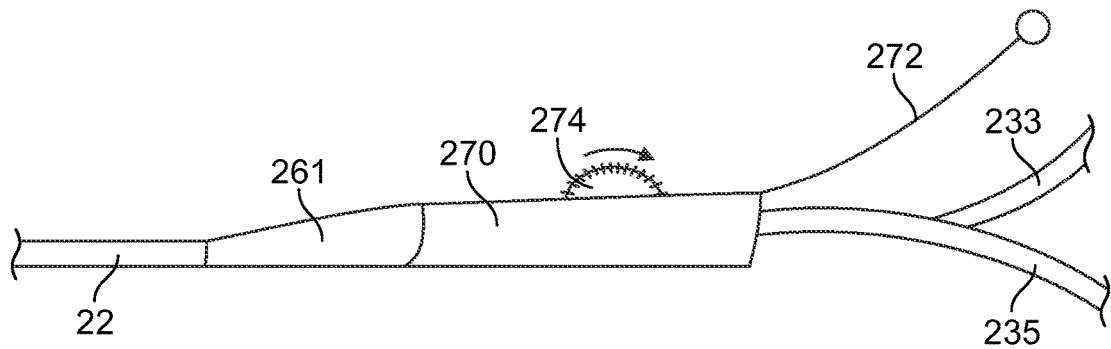
Figure 15G:
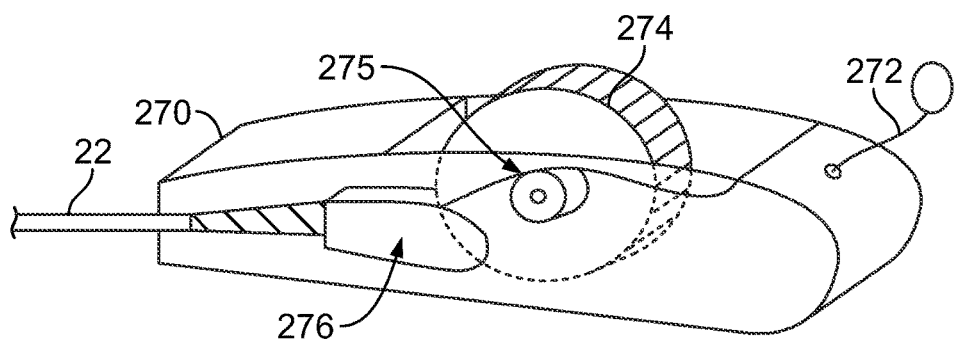

An alternative embodiment of the proximal hub member 270 is shown in FIG. 15f, which includes a thumb wheel 274 rotatably coupled with the proximal hub member 270 and the access wire 272, whereby rotational movement of the thumb wheel 274 pulls the access wire 272 proximally to pull the wires 60 in the multi-lumen sheath 22 to retract the deployed filter member 16. Alternatively, the access wire 272 may be pushed distally by rotation of the thumb wheel 274 as to displace the wires 60 distally in the multi-lumen sheath 22 for deployment of the filter member. As shown in FIG. 15g, the thumb wheel 274 may be rotatably coupled with a central axis portion 275 to displace the access wire 272 proximally and distally. Alternatively, the thumb wheel 274 may located within a removable shell portion, such that the proximal end 276 of the multi-lumen sheath 22 may be removably coupled with the proximal hub member 270.

Figure 15H:
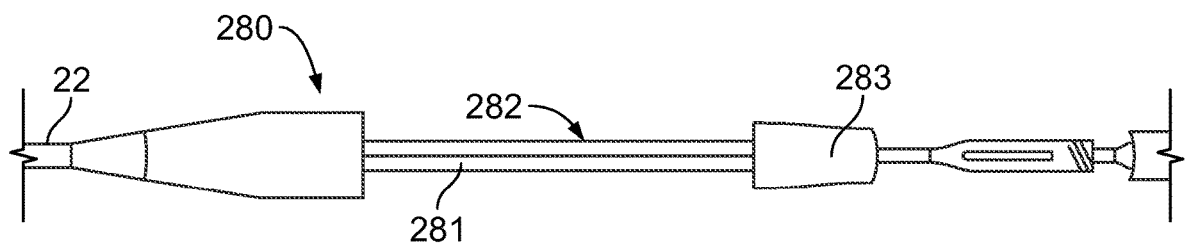

An alternative proximal hub member to deploy the wires 60 within the multi-lumen sheath 22 is shown in FIG. 15h, whereby the proximal hub member 280 includes a hypotube stylet 281 that supports a guidewire line 282 during deployment of the filter member 16. A proximal hub portion 283 is slidably coupled with the hypotube stylet 281 and the guidewire line 282, such that the proximal hub portion 283 slides to deploy the wires 60 distally for the filter member deployment.

Figure 15I:
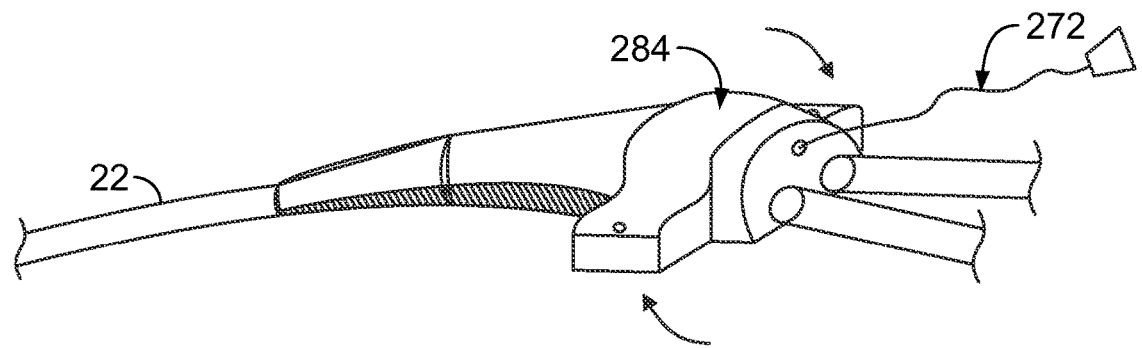

An alternative proximal hub member to deploy the wires 60 within the multi-lumen sheath 22 is shown in FIG. 15i, whereby the proximal hub member includes a rotatably suture wing 284 operably coupled with the access wire 272 to displace the wires 60 proximally and distally by rotation of the suture wing 284 about its axis.

Figure 15J:
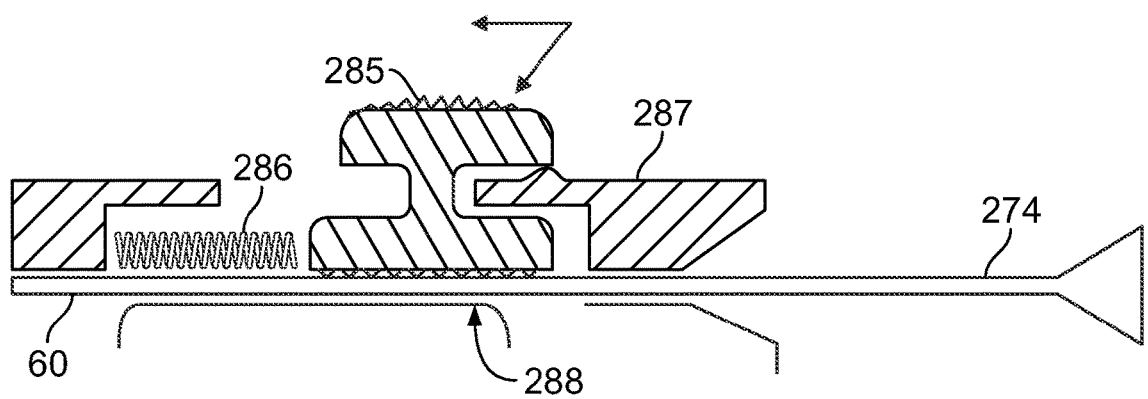

An alternative proximal hub member to deploy the wires 60 within the multi-lumen sheath 22 is shown in FIG. 15j, whereby the proximal hub member includes a return tab 285 operably coupled with a spring 286 to push the access wire 274 in an inchworm fashion proximally and distally to displace wires 60 and deploy the filter member. The return tab 285 may be pushed down and forward to move the wires 60 and releasing the tab 285 allows the tab to retract and abut a bump portion 287 of the proximal hub member. In one embodiment, the access wire 274 may be operably coupled to a bearing surface 288 to allow the wire 274 to longitudinally move within the proximal hub member.

Figure 15K:
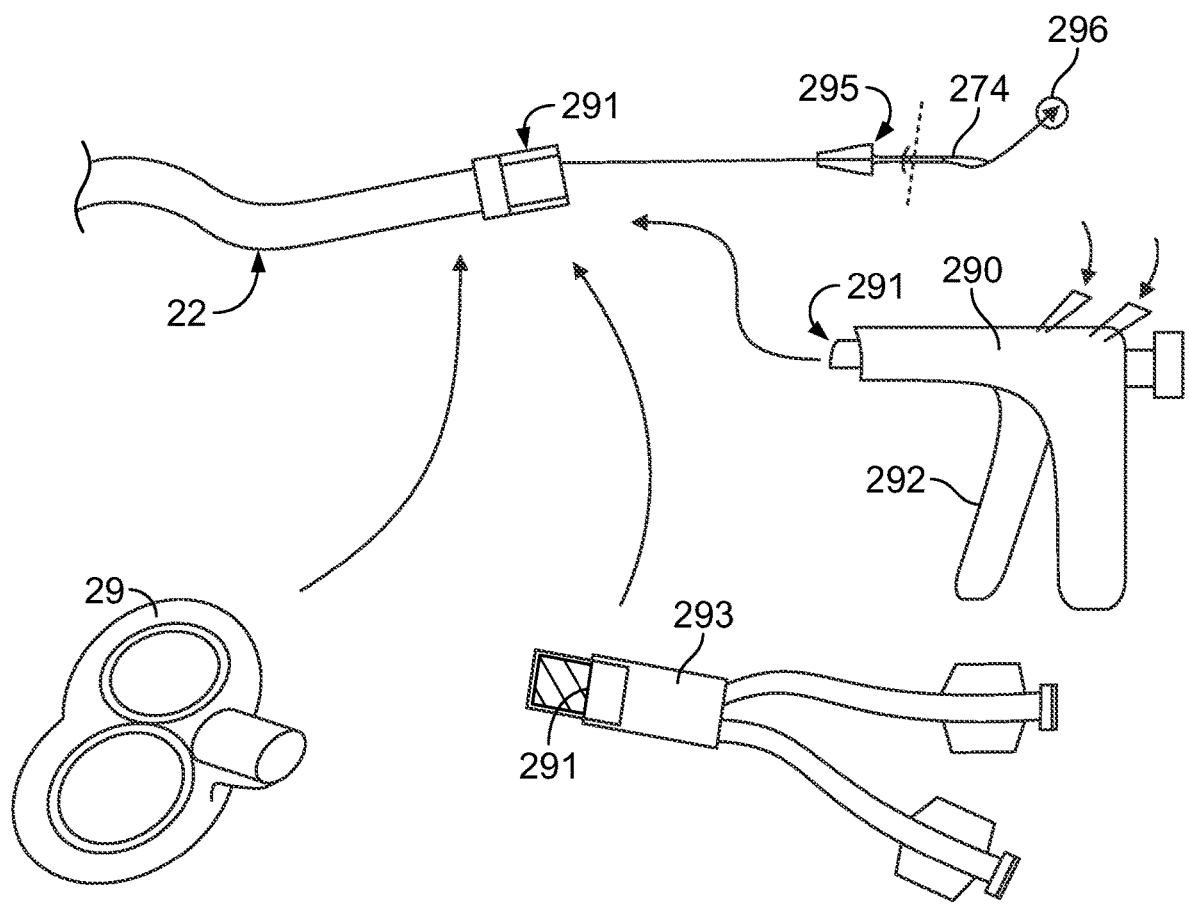

An alternative proximal hub member to deploy the wires 60 within the multi-lumen sheath 22 is shown in FIG. 15k, whereby the proximal hub member includes a removable handle 290 operably coupled to a connector 291 on the proximal end of the multi-lumen sheath 22 to deploy the wires 60 and proximally and distally move the access wire 274. A trigger 292 may operate to displace the access wire 274 proximally and distally. Alternatively, the connector 291 on the proximal end of the multi-lumen sheath 22 may be operably coupled with a wire connector or extension lines 293 to allow retrieval of the access wire 274 and the filter member. Alternatively, the connector 291 on the proximal end of the multi-lumen sheath 22 may be operably coupled to an implantable port 294. Alternatively, a cut-to-length wire 295 with a crimp on bead 296 to fix the access wire 274 in place at a desired position. The bead could become lodged in the removable access device to allow retrival of the filter.

Figure 16A:
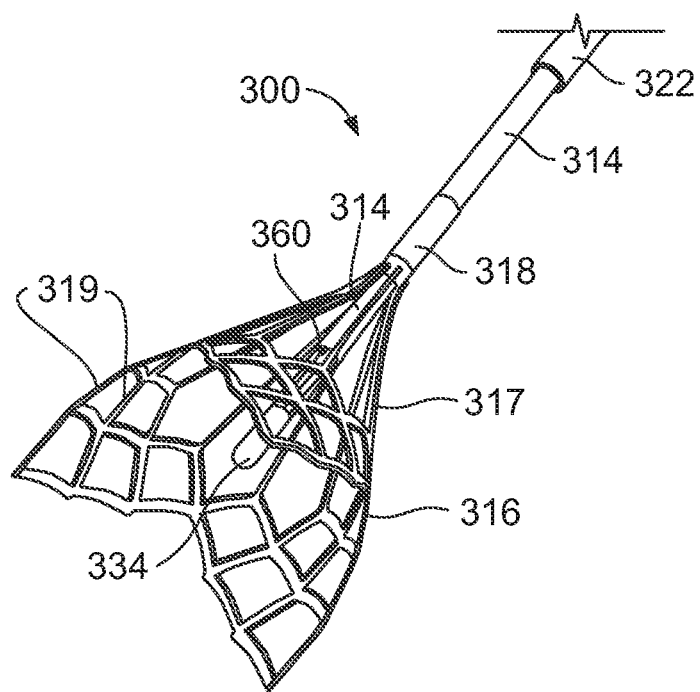
FIGS. 16A and 16B are perspective views of a filter member mounted at a distal end of a central line catheter having a distal balloon.
Figure 16B:
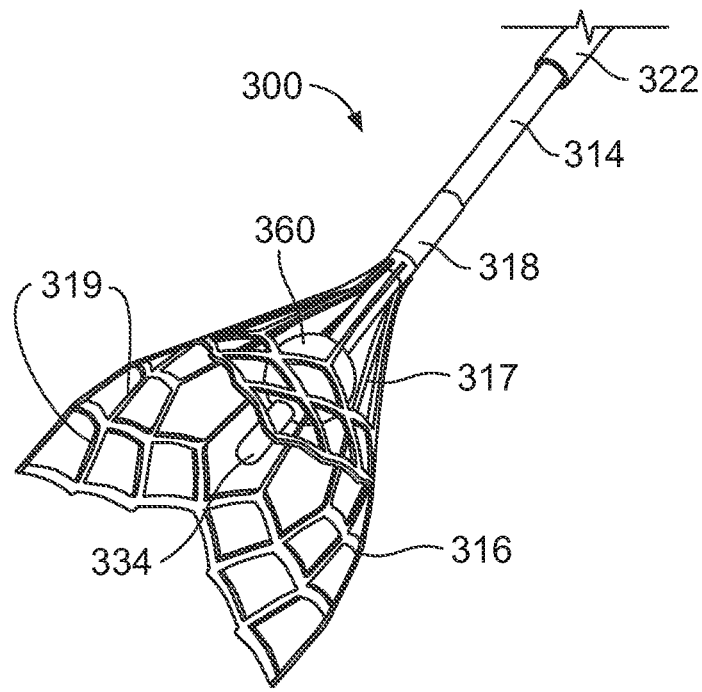

FIGS. 16A-16B depict an alternative embodiment of the filter member 216, having first end 318, first structural elements 317 and second structural elements 319. Filter member 300, however, employs a modified distal end 314 of the catheter 312 to include an expansive balloon 360. The guidewire lumen of the multi-lumen catheter 312 may be used in place of a distal port for either condition sensing, flushing, infusion or the like. The expansive balloon 360 may be used to break up thrombus captured within the filter member 316, either by mechanical force through serial dilatation or by infusion of a thrombolytic agent through openings in the balloon 360. FIG. 16A depicts the balloon 360 in its collapsed state, whereas FIG. 16B depicts the balloon in its expanded state.

Alternatively, an expansive balloon 360 may be placed proximal the filter member 300 and serve to temporarily occlude the vessel to facilitate aspiration or evacuation of thrombus from the filter member 30.

Figure 17A:
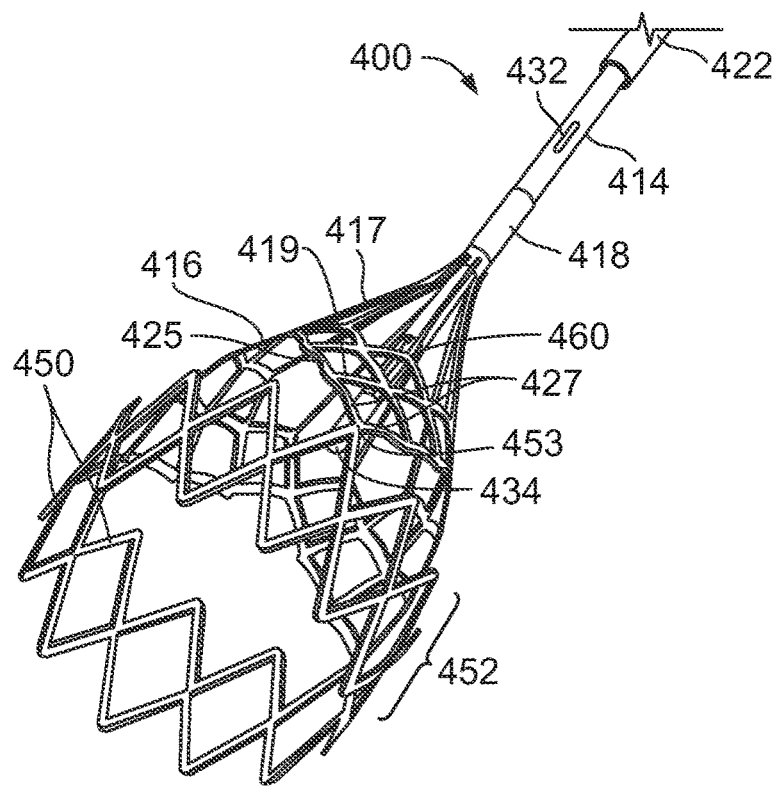
FIGS. 17A and 17B are perspective views of an alternative embodiment of a filter member mounted at a distal end of a central line catheter having a distal balloon.
Figure 17B:
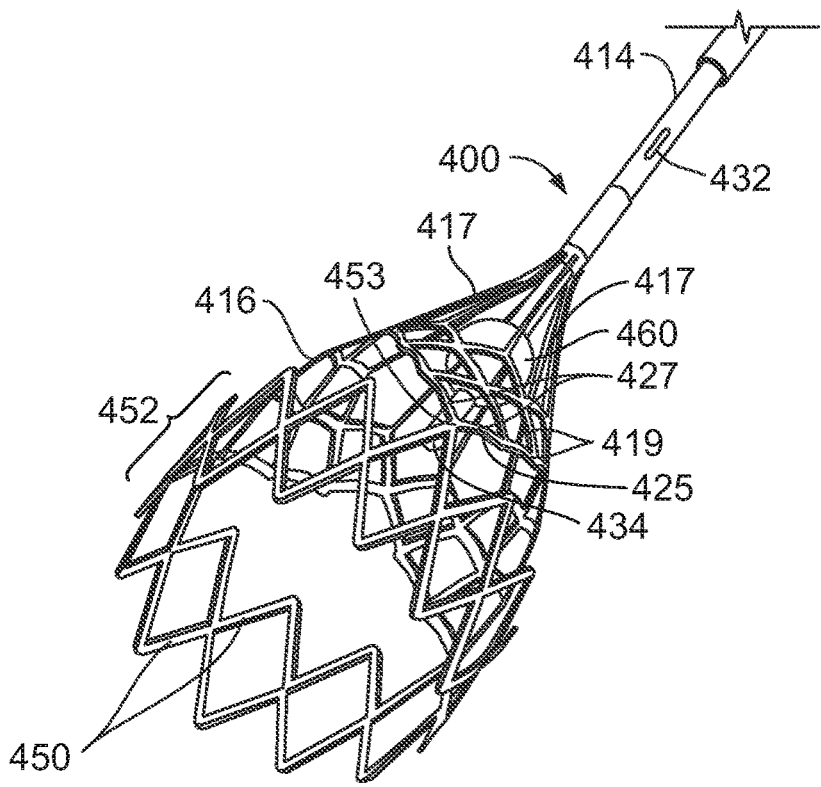

FIGS. 17A-17B depict an alternative embodiment of the filter member 216 having first end 418, first structural elements 417 and second structural elements 419, at least one circumferential ring member 452 connected to the terminal apex member 427 of each of the petal-like members 425 at a juncture 453 with the terminal apex member 427. Filter member 400, however, employs a modified distal end 414 of the catheter 412 to include an expansive balloon 460. The guidewire lumen of the multi-lumen catheter 412 may be used in place of a distal port for either condition sensing, flushing, infusion or the like. The expansive balloon 460 may be used to break up thrombus captured within the filter member 416, either by mechanical force through serial dilatation or by infusion of a thrombolytic agent through openings in the balloon 460.

FIGS. 18A-18B depict an alternative embodiment of the filter member 16 operably coupled with the wires 60 disposed within the multi-lumen sheath 22 to be deployed or expanded by the distal movement of the wires 60. In FIG. 18A, the wires 60 expand to a generally spiral configuration 500, whereby the wires 60 transition to a large spiral strut 502 and then the large spiral struts 502 transition to a smaller spiral struts 504 to distally connect to a single distal end 506. In FIG. 18b, the wires 60 expand upon distal movement and are tethered to an expandable filter member 510 that parachutes to the expanded state upon distal movement of the wires 60 or upon distal movement of centrally located rod or shaft which is sufficiently rigid to withstand buckling. The expandable filter member 510 connects at a distal end 512 to promote the parachuting effect of the filter member 510.

Again, an expansive balloon 460 may be positioned proximal the filter member 416 to permit temporary occlusion of the blood vessel and permit aspiration or evacuation of thrombus from the filter member 416.

Additionally, flow sensors and/or pressure transducers in operable association with each ports or portions of the wire body, multi-lumen sheath, or wire capsule, with the associated electrical connections to the flow sensors an/or pressure transducers passing through the respective lumens associated with each port and terminating at the proximal end of the catheter body 12. Where flow sensors are employed, a single flow sensor associated with proximal port, the distal port or the distal end of outer sheath 22 may be sufficient to detect fluid flow rate at the position of the body 12. By providing a flow sensor at the distal end of sheath 22, the clinician will be able to determine flow velocity at the distal end of the outer sheath 22 prior to introducing the body 12 and make fine adjustments to the placement of the distal end of the outer sheath 22 to ensure proper placement for the filter member 16. Plural flow sensors may be employed and operably associated with each of proximal port and distal port to sense changes in flow velocity across the filter member 16. Alternatively, the flow sensors and/or pressure transducers may reside in communication with the lumens respectively associated with each port at the proximal end of the catheter body, thereby eliminating the need for electrical connectors resident with the associated lumens. Furthermore, wireless flow sensors and/or pressure transducers may be provided in communication with each port, and be operably coupled to a power source and a transmitter to wirelessly transmit telemetry data from the transducers to a wireless receiver in communication with the transmitter, as is known in the art.

Thus there has been described a central venous access filter in accordance with the foregoing embodiments of the invention which include, generally, a multi-lumen catheter body, a filter member and a multi-lumen sheath. The multi-lumen sheath and/or catheter body that has a plurality of ports each of which are in fluid flow communication with at least one lumen in the multi-lumen catheter body. Lumens may include a central guidewire lumen useful for tracking over a guidewire and/or larger volume infusion of bioactive agents, intravenous fluids, blood transfusions, or other fluids; infusion lumens in communication with infusion ports positioned to direct fluids to the space bounded by the filter member for introducing bioactive agents, including thrombolytic agents or flushing agents, including pressurized fluids for mechanical thrombolysis directly to the capture site of the thrombus in the filter member; and lumens communicating with proximal and distal ports which may also be used for fluid introduction and/or may house or communicate with sensors, such as pressure transducers, flow sensors, analyte sensors, color sensors, optical sensors or the like. The filter member may be detachable from the multi-lumen catheter body to permit temporary filter placement and later retrieval by a detachment mechanism that cooperates between the filter and the multi-lumen catheter body. These and other aspects of the present invention are provided by way of non-limiting examples, with the claims appended hereto serving to define the scope of the subject matter regarded as the invention.

What is claimed is:

1. A medical device, comprising:
   a. a sheath having a generally tubular wall and having a primary central lumen and a plurality of secondary lumens, at least two lumens of the plurality of secondary lumens passing through at least a partial longitudinal aspect of the sheath and either within or adjacent to the generally tubular wall and including a wire body longitudinally disposed and translatable within at least one of the at least two of a plurality of secondary lumens;
   b. a filter capsule extending from and coupled to a distal end of the sheath and disposed over the wire body, the filter capsule having a single lumen; and
   c. a filter member having a proximal end fixedly attached to a distal end of the wire body and the distal end of the filter member and the wire body are received within the filter capsule when the filter member is in a diametrically collapsed state, the filter member also having a diametrically enlarged state, wherein the filter member is deployable to its diametrically enlarged state from or retrievable in its diametrically collapsed state into the filter capsule upon translation of the wire body within the at least one of the at least two of a plurality of secondary lumens and along a longitudinal axis of the sheath.

2. The medical device according to claim 1, wherein the sheath further comprises a proximal port and a distal port associated with each of the at least two lumens of the plurality of secondary lumens.

3. The medical device according to claim 2, wherein the wire body passes through the proximal port and the distal port of at least one lumen of the at least two lumens of the plurality of secondary lumens.

4. The medical device according to claim 2, wherein the sheath further includes a plurality of openings associated with the at least two lumens of the plurality of secondary lumens along the longitudinal length of the sheath.

5. The medical device according to claim 1, wherein at least one lumen of the at least two lumens of the plurality of secondary lumens further comprises an infusion lumen having at least one infusion port.

6. The medical device according to claim 5, wherein the wire body is disposed within the infusion lumen and the at least one infusion port further comprises a plurality of infusion ports arrayed along a longitudinal axis and a circumferential axis of the infusion lumen and about the wire body.

7. The medical device according to claim 1, wherein the filter member further comprises a plurality of structural members configured to form a plurality of proximal interstitial openings and distal interstitial openings, the proximal interstitial openings being larger in open surface area than the distal interstitial openings.

8. The medical device according to claim 1, wherein one lumen of the at least two lumens of the plurality of secondary lumens further comprises a central lumen, and the sheath further has a wall bounding the central lumen, the wall having a wall thickness, and at least a second lumen of the at least two lumens of the plurality of secondary lumens being at least partially within the wall thickness, and at least a second wire body disposed within the at least second lumen of the at least two lumens of the plurality of secondary lumens, wherein the filter member is coupled with distal ends of the wire body and the at least a second wire body.

9. The medical device of claim 8, wherein the filter member is expanded to the diametrically enlarged state when at least one of the wire body or at least second wire body is translated distally from a distal portion of the sheath.

10. The medical device of claim 9, further comprising a proximal hub member operably coupled with a proximal end of the sheath; an access wire operably coupled with the proximal ends of the wire body and the at least second wire body; an actuator operably coupled with the access wire to longitudinal displace the access wire and at least one of the wire bodies distally thereby distally translating the filter member.

11. The medical device according to claim 1, wherein the primary central lumen has a transverse cross-sectional area greater than a transverse cross-sectional area of any one of the at least two of a plurality of secondary lumens.

* * * * *